United States Patent
Kagawa et al.

(10) Patent No.: US 12,376,732 B2
(45) Date of Patent: Aug. 5, 2025

(54) DISPLAY CONTROL APPARATUS, DISPLAY CONTROL METHOD, AND NON-TRANSITORY RECORDING MEDIUM ON WHICH DISPLAY CONTROL PROGRAM IS RECORDED

(71) Applicant: OLYMPUS CORPORATION, Hachioji (JP)

(72) Inventors: Hiroaki Kagawa, Hachioji (JP); Osamu Nonaka, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 459 days.

(21) Appl. No.: 17/863,559

(22) Filed: Jul. 13, 2022

(65) Prior Publication Data

US 2022/0338713 A1    Oct. 27, 2022

Related U.S. Application Data

(63) Continuation of application No. PCT/JP2020/000855, filed on Jan. 14, 2020.

(51) Int. Cl.
*G16H 20/40* (2018.01)
*A61B 1/00* (2006.01)
(Continued)

(52) U.S. Cl.
CPC .............. *A61B 1/0005* (2013.01); *A61B 1/05* (2013.01); *A61B 1/3132* (2013.01)

(58) Field of Classification Search
CPC ....... A61B 1/0005; A61B 1/05; A61B 1/3132; A61B 2034/2048; A61B 2090/371; A61B 90/361; G16H 20/40; G16H 40/63
See application file for complete search history.

(56) References Cited

U.S. PATENT DOCUMENTS

2013/0109916 A1* 5/2013 Levy .................. A61B 1/00181
600/109
2014/0320617 A1   10/2014 Parks et al.
(Continued)

FOREIGN PATENT DOCUMENTS

JP    58-29439 A    2/1983
JP    8-18861 A     1/1996
(Continued)

OTHER PUBLICATIONS

International Search Report dated Mar. 31, 2020, issued in counterpart International Application No. PCT/JP2020/000855 (3 pages).

*Primary Examiner* — Samantha (Yuehan) Wang
(74) *Attorney, Agent, or Firm* — WHDA, LLP

(57) ABSTRACT

A display control apparatus includes a processor, and the processor determines, in work on an object within a space, which one of a first picked-up image by a first image pickup device disposed at a first predetermined position within the space and a second picked-up image by a second image pickup device disposed at a second predetermined position different from the first predetermined position within the space is appropriate for confirmation of procedure in a state associated with the work on the object using a treatment instrument, outputs a determination result and controls display using at least one of the first picked-up image or the second picked-up image based on the determination result.

25 Claims, 24 Drawing Sheets

(51) Int. Cl.
*A61B 1/05* (2006.01)
*A61B 1/313* (2006.01)

(56) References Cited

U.S. PATENT DOCUMENTS

| | | | |
|---|---|---|---|
| 2017/0105608 A1 | 4/2017 | Kura et al. | |
| 2017/0205619 A1 | 7/2017 | Hamada et al. | |
| 2021/0152747 A1* | 5/2021 | Takai | G06F 3/04845 |
| 2021/0278904 A1* | 9/2021 | Ma | G06F 3/04847 |

FOREIGN PATENT DOCUMENTS

| | | |
|---|---|---|
| JP | 9-5643 A | 1/1997 |
| JP | 2000-32442 A | 1/2000 |
| JP | 4121845 B2 | 7/2008 |
| JP | 2010-178766 A | 8/2010 |
| JP | 2015-119827 A | 7/2015 |
| JP | 2015-533300 A | 11/2015 |
| JP | 2016-522022 A | 7/2016 |
| JP | 2017-227941 A | 12/2017 |
| JP | 6256872 B2 | 1/2018 |
| WO | 2014/061023 A1 | 4/2014 |
| WO | 2014/179236 A1 | 11/2014 |
| WO | WO-2015/146836 A1 * | 10/2015 |
| WO | 2015/198981 A1 | 12/2015 |
| WO | 2016/072395 A1 | 5/2016 |
| WO | 2016/111178 A1 | 7/2016 |

* cited by examiner

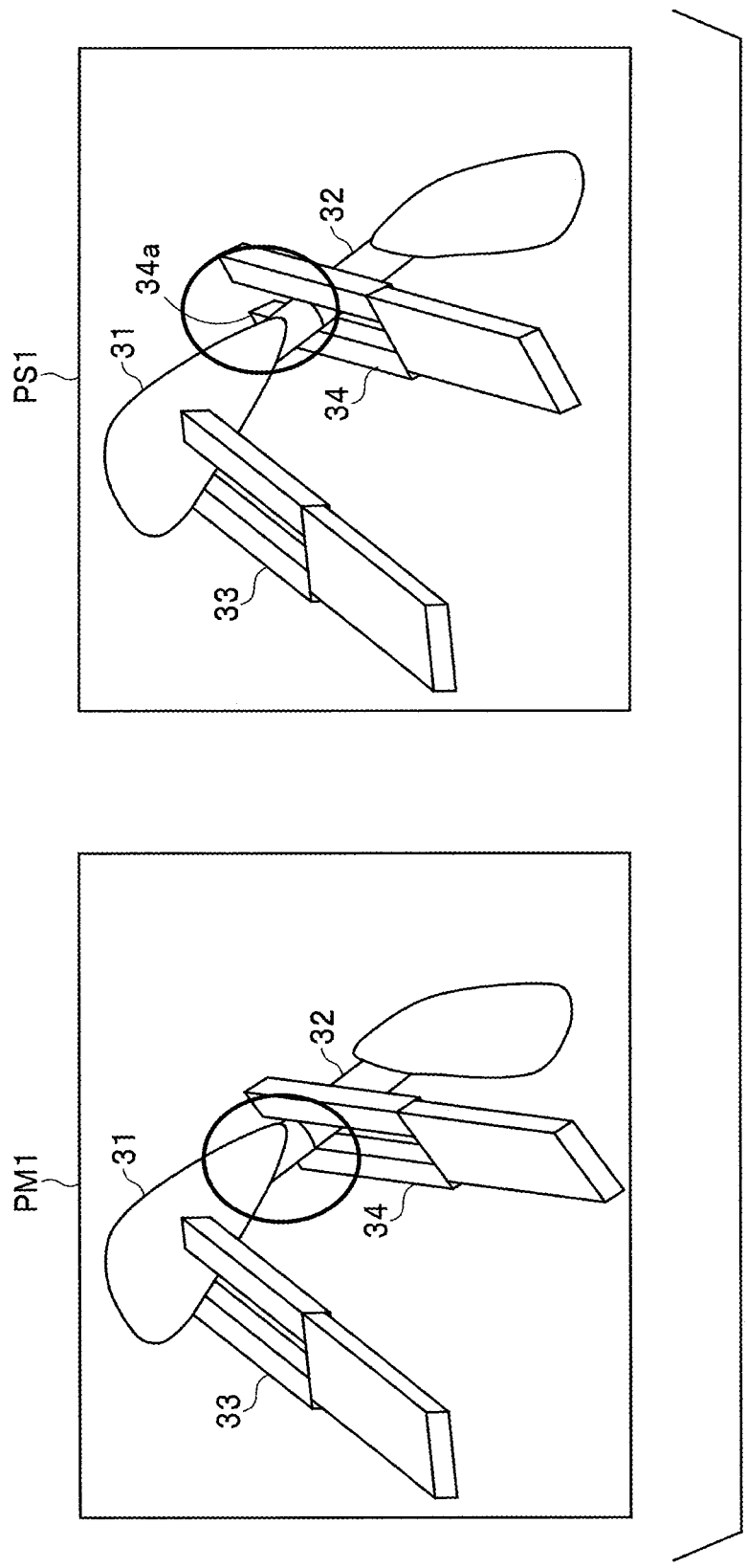

FIG. 3

| SCENE | MAIN IMAGE IS APPROPRIATE | UTILIZATION OF SUB IMAGE IS APPROPRIATE |
|---|---|---|
| FMD | FIXED POSITION | MOTION OF CONFIRMATION |
| TREATMENT INSTRUMENT | DURING INSERTION 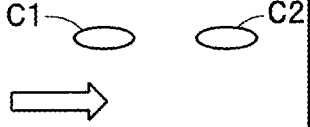 DISTAL END IS SMALL 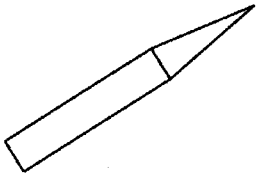 | BEFORE PINCHING 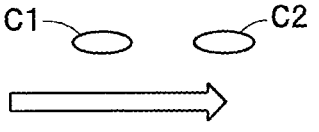 DISTAL END IS LARGE 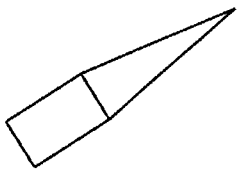 |
| EXTERNAL CAMERA | BASIC POSTURE, BASIC OPERATION | CONFIRMATION POSTURE, CONFIRMATION OPERATION |
| ENDOSCOPE APPARATUS | DURING INSERTION, DURING BENDING | DURING CONFIRMATION |
| AFFECTED AREA | DURING EXPLORATION<br>SMALL 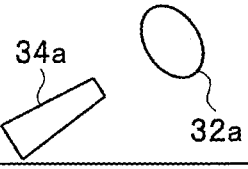 | PROCEDURE IS STARTED<br>LARGE 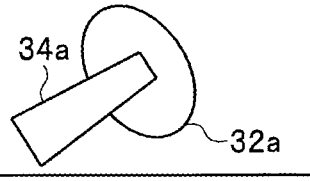 |
| MEDICAL PHASE | ACCESSING TARGET PORTION | CONFIRMATION WORK |
| CONDITION DETERMINATION UNIT | SELECT FIRST DISPLAY MODE | SELECT SECOND DISPLAY MODE |
| DISPLAY UNIT | DISPLAY MAIN IMAGE | DISPLAY SUB IMAGE |

FIG. 19
FIRST PICKED-UP IMAGE
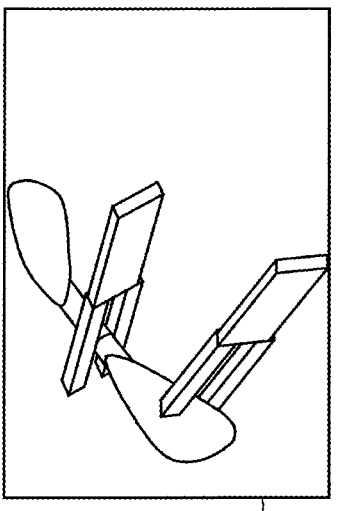
13IS
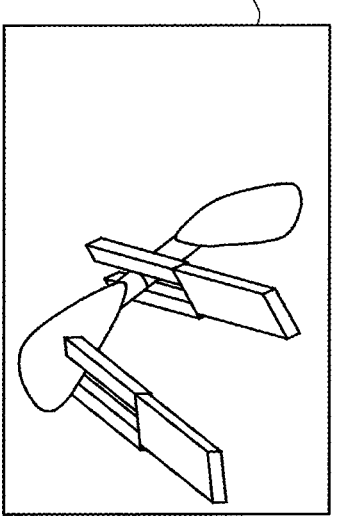
15IS
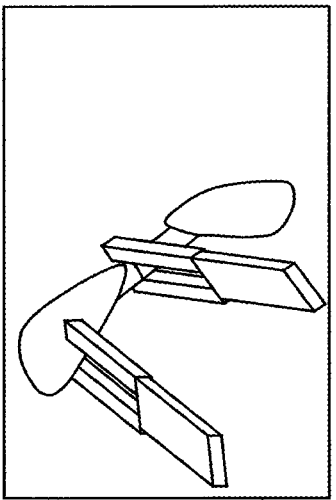
PM3
SECOND PICKED-UP IMAGE
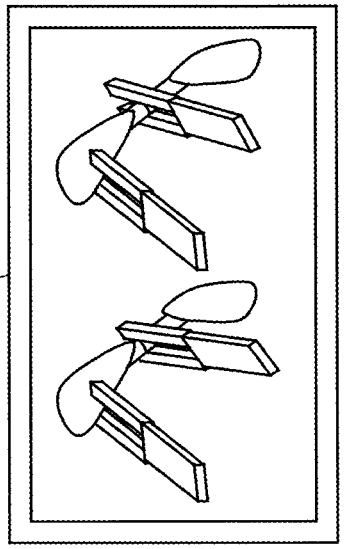
66IS
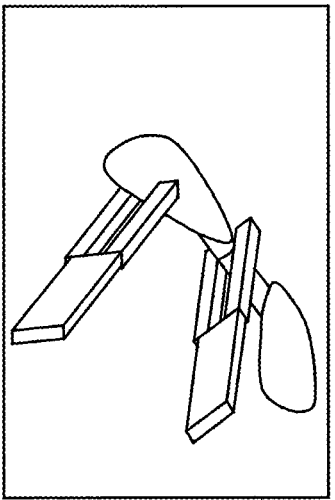
63IS
PS3

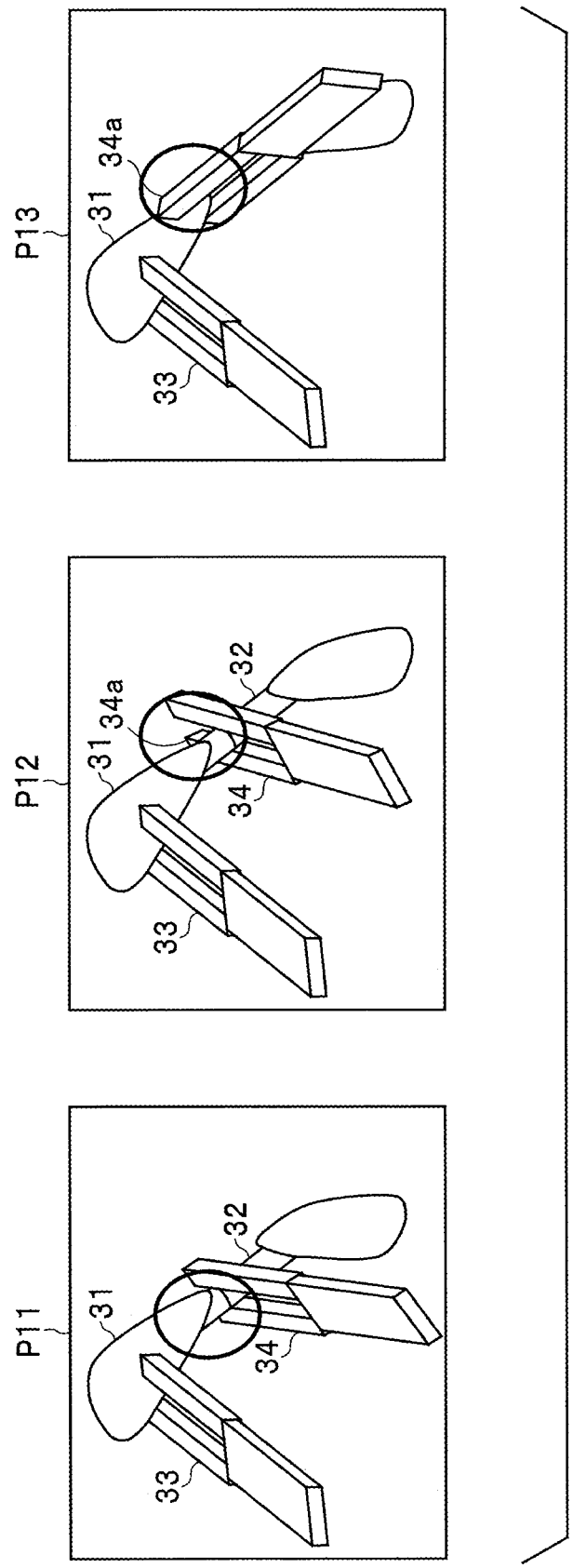

DISPLAY CONTROL APPARATUS, DISPLAY CONTROL METHOD, AND NON-TRANSITORY RECORDING MEDIUM ON WHICH DISPLAY CONTROL PROGRAM IS RECORDED

CROSS REFERENCE TO RELATED APPLICATION

This application is a continuation application of PCT/JP2020/000855 filed on Jan. 14, 2020, the entire contents of which are incorporated herein by this reference.

BACKGROUND OF THE INVENTION

1. Field of the Invention

The present invention relates to a display control apparatus that facilitates procedure utilizing an endoscope, or the like, a display control method, and a non-transitory recording medium on which a display control program is recorded.

2. Description of the Related Art

In related art, an endoscope for medical use has been widely used which, by inserting an elongated insertion portion into a body cavity observes organs, and the like, in a deep portion inside the body cavity without dissecting a body surface and performs various kinds of treatment, procedure, and the like, using a treatment instrument inserted into a treatment instrument channel of the insertion portion of the endoscope as necessary.

Further, for the purpose of achieving less invasiveness to a patient, a laparoscopic surgery (hereinafter, also referred to as a surgery) in which treatment procedure is performed without opening an abdominal cavity is also performed. In the surgery, an endoscope for observation (endoscope for surgery) is inserted into a body cavity through a trocar that punctures an abdominal area of the patient. A surgeon can perform procedure that is less invasive by utilizing an observation image obtained by the endoscope.

As an endoscope system using such an endoscope, for example, there is art apparatus disclosed in Japanese Patent No. 6256872. The apparatus, which employs a plurality of cameras, enables display of images obtained by the respective cameras at different monitors at the same time. Further, the apparatus is configured so as to be able to direct respective line-of-sight directions of the plurality of cameras to the same gaze position in accordance with an instruction by an observer who designates the gaze position.

SUMMARY OF THE INVENTION

A display control apparatus according to one aspect of the present invention includes a processor, in which the processor is configured to determine, in work on an object within a space, which one of a first picked-up image by a first image pickup device disposed at a first predetermined position within the space and a second picked-up image by a second image pickup device disposed at a second predetermined position different from the first predetermined position within the space is appropriate for confirmation of procedure in a state associated with the work on the object rising a treatment instrument and output a determination result, and control display using at least one of the first picked-up image or the second picked-up image based on the determination result.

A display control method according to one aspect of the present invention includes determining, in work on an object within a space, which one of a first picked-up image by a first image pickup device disposed at a first predetermined position within the space and a second picked-up image by a second image pickup device disposed at a second predetermined position different from the first predetermined position within the space is appropriate for confirmation of procedure in a state associated with the work on the object using a treatment instrument and outputting a determination result, and controlling display using at least one of the first picked-up image or the second picked-up image based on the determination result.

A non-transitory recording medium on which a display control program is recorded according to one aspect of the present invention has the display control program causing a computer to execute: determining, in work on an object within a space, which one of a first picked-up image by a first image pickup device disposed at a first predetermined position within the space and a second picked-up image by a second image pickup device disposed at a second predetermined position different from the first predetermined position within the space is appropriate for confirmation of procedure in a state associated with the work on the object using a treatment instrument and outputting a determination result, and controlling display using at least one of the first picked-up image or the second picked-up image based on the determination result.

BRIEF DESCRIPTION OF THE DRAWINGS

FIG. 2A is an explanatory diagram for explaining scenes where a first display mode and a second display mode are to be employed;

FIG. 3 is an explanatory diagram for explaining a method for determining a condition by a condition determination circuit;

FIG. 19 is an explanatory diagram for explaining display on a plurality of monitors and an FMD;

FIG. 29 is an explanatory diagram for explaining operation of the apparatus in FIG. 28.

DETAILED DESCRIPTION OF THE PREFERRED EMBODIMENTS

Embodiments of the present invention will be described in detail below with reference to the drawings.

First Embodiment

Figure 1:
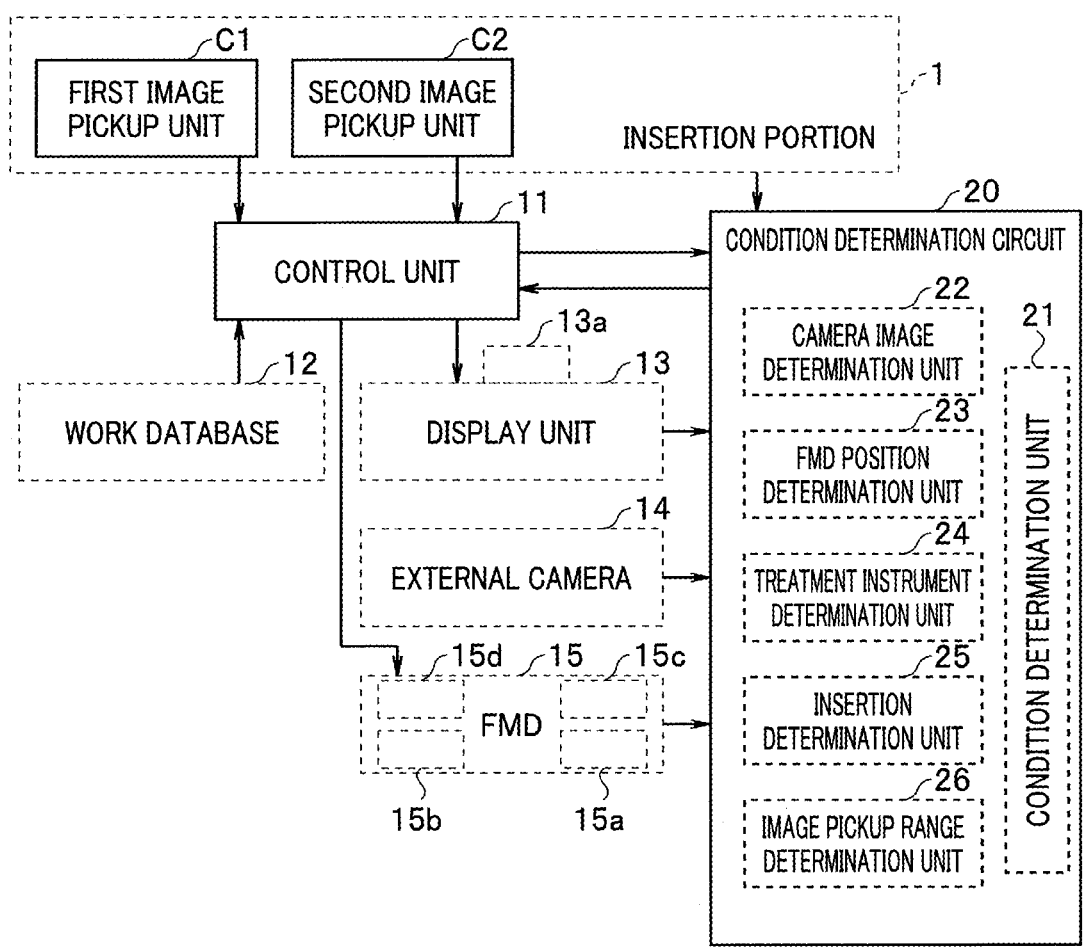
FIG. 1 is a block diagram illustrating a display control apparatus according to a first embodiment of the present invention.

FIG. 1 is a block diagram illustrating a display control apparatus according to a first embodiment of the present invention. While an example where the present invention is utilized in procedure within an abdominal cavity in an endoscope system using an endoscope will be described the first embodiment, the present invention can be applied to various apparatuses that observe a work status, and the like, by utilizing picked-up images from a plurality of cameras, as well as the endoscope system.

In the present embodiment, display is performed using a plurality of picked-up images which are acquired by a plurality of image pickup units and which have image pickup ranges different from each other. For example, display is performed using a first picked-up image that is a moving image or a still image acquired by a first image pickup unit and a second picked-up image that is a moving image or a still image acquired by a second image pickup unit that performs image pickup in an image pickup range different from an image pickup range of the first image pickup unit. The first picked-up image is to be used for display in conditions of a normal surgery, work, and the like, and may be referred to as, for example, a main image. Further, the second picked-up image is to be used for display in a necessary scene and may be referred to as, for example, a sub image. In a case where the images are employed in a laparoscopic surgery, or the like, using an endoscope, the first picked-up image (main image) may be used, for example, during insertion, and the second picked-up image (sub image) in be used, for example, in a necessary scene during procedure. Further, the first and the second picked-up images may be used in inverse scenes.

In the present embodiment, a mode can be automatically switched between a first display mode in which display is performed only with the first picked-up image and a second display mode in which display of the second picked-up image is performed, by using a condition determination circuit that determines a condition of work such as a surgery (hereinafter, referred to as condition determination).

First, a scene in which the second display mode in which display is performed with the second picked-up image is required will be described with reference to FIG. 2A. FIG. 2A is an explanatory diagram for explaining scenes where the first display mode and the second display mode are to be employed.

A left part of FIG. 2A illustrates the first picked-up image (main image), and a right part of FIG. 2A illustrates the second picked-up image (sub image). A main image PM1 and a sub image PS1 illustrated in FIG. 2A are respectively acquired by the first image pickup unit and the second image pickup unit at the same timing. In other words, the main image PM1 and the sub image PS1 are images of an aspect where an organ 31 is pinched with a forceps 33, and predetermined procedure such as, for example, clipping, dissection and cauterization is performed on a lumen 32 leading to the organ 31 with a treatment instrument 34 and are the images that are picked up at the same time by the first and the second image pickup units.

The first image pickup unit and the second image pickup unit have different image pickup ranges and have different operative fields that can be observed particularly in portions indicated with thick frames in FIG. 2A. In other words, the main image PM1 does not include a distal end portion of the treatment instrument 34. In contrast, as indicated by a thick frame portion, the sub image PS1 includes a distal end portion 34a of the treatment instrument 34, and an image of a state where the lumen 32 is surely pinched with the treatment instrument 34 is picked up. The surgeon can determine that the state becomes a state where the procedure can be surely performed by the treatment instrument 34 by observing the sub image PS1.

In other words, in the example in FIG. 2A, a scene where display in the second display mode is required is a scene where when the surgeon pinches the lumen 32 with the treatment instrument 34, a distal end of the treatment instrument 34 cannot be confirmed in the first display mode in which the main image PM1 is displayed. Alternatively, the scene where display in the second display mode is required is a scene where when the surgeon pinches the lumen 32 with the treatment instrument 34, the distal end of the treatment instrument 34 can be confirmed with the sub image PS1 in the example in FIG. 2A.

In other words, the scene where display in the second display mode is required in the example in FIG. 2A is a scene where the surgeon performs work of confirming a status of work on an object, in which case, the surgeon can determine that procedure can be surely performed by performing display in the second display mode in which the sub image PS1 is displayed. Note that display is performed in the first display mode in a case where the surgeon performs work other than confirmation work (hereinafter, also referred to as "basic work").

In the present embodiment, a scene where the second display mode is required is determined by condition determination by the condition determination circuit outputs of various kinds of sensors.

FIG. 1, the display control apparatus includes a control unit 11. The control unit 11 may be constituted with a processor using a CPU (central processing unit), an FPGA (field programmable gate array), or the like, may operate in accordance with a program stored in a memory (not illustrated) to control respective units or may implement part or all functions with a hardware electronic circuit. The control unit 11 controls respective units of the display control apparatus.

FIG. 1 illustrates an example where the display control apparatus is applied to an endoscope system, and the first and the second image pickup units are provided in an insertion portion 1 of an endoscope. The endoscope is constituted with, for example, a rigid endoscope having a rigid insertion portion 1 or an endoscope with a flexible distal end in which a distal end of the insertion portion can be curved, and a first image pickup unit C1 and a second image pickup unit C2 are disposed on the distal end side of the insertion portion 1. Note that an illumination optical system constituted with a light guide, and the like, a wiring, and the like, that transmit a subject image (picked-up image) are also disposed within the insertion portion 1.

The first image pickup unit and the second image pickup unit as sensors are image pickup devices including image pickup elements such as a CCD (charge-coupled device) and a CMOS (complementary metal-oxide-semiconductor) sensor (not illustrated) and perform photoelectric conversion on an optical image from a subject to acquire picked-up images. While the picked-up images are subjected to image processing by a camera control unit connected to the endoscope and supplied to the display control apparatus, to simplify the drawing. FIG. 1 illustrates a state as if the picked-up images from the first and the second image pickup units C1 and C2 were directly supplied to the control unit 11.

The insertion portion 1 passes through a trocar (not illustrated) and is disposed within an abdominal cavity of a patient, or the like. Images of inside of the abdominal cavity are picked up by the first image pickup unit C1 and the second image pickup unit C2 in this manner, and the first and the second picked-up images that are picked-up images of inside of the abdominal cavity are supplied to the control unit 11. The control unit 11 provides the acquired first and second picked-up images to the condition determination circuit 20.

Note that while in the present embodiment, an example where the image pickup units C1 and C2 are provided in the insertion portion 1 has been described because the present invention is applied to the endoscope system, also in a case where the present invention is applied to a system other than the endoscope system, the first and the second image pickup units are preferably disposed in some member such as, for example, an insertion member, and the first and the second image pickup units preferably move at the same time in association with movement of the member. By this means, also in a case where observation is performed at a relatively narrow location such as a lumen, it is possible to dispose the first and the second image pickup units within the lumen in a state where an observation target portion and periphery of the observation target portion are relatively easily captured in image pickup ranges of the first and the second image pickup units, by disposing an insertion member, or the like, within the lumen.

A work database 12 is constituted with a predetermined storage medium such as a hard disk and a semiconductor memory and is a database that stores various kinds of information regarding work, or the like, that utilizes display of the first and the second picked-up images, which are information to be utilized for condition determination by the condition determination circuit 20. For example, information regarding a series of processing procedure of work and various kinds of information in respective scenes during work may be stored.

An external camera 14 is an image pickup apparatus disposed in a surgery room, a work room, or the like, and can pick up an image, for example, having an image pickup range of a region including a region where the surgeon (observer) exists. The external camera 14 may be constituted so as to be able to pick up an image of only part of the surgeon (observer), for example, a face portion (head portion) and periphery of the face portion (head portion). The picked-up image by the external camera 14 is supplied to the condition determination circuit 20. Further, the external camera 14 may be constituted so as to be able to pick up an image of a hand portion of the surgeon who grasps the treatment instrument or a portion near the insertion portion to be inserted into a body cavity.

A display unit 13 is a display constituted with an LCD (liquid crystal) panel, or the like, and displays the picked-up images supplied from the control unit 11 on a display screen. Note that a camera 13a may be attached to the display unit 13, the camera 13a may be able to pick up an image of a region including the surgeon (observer) and may be able to supply the picked-up image by the camera 13a to the condition determination circuit 20.

A face mounted display (FMD) 15, which is a display apparatus (also referred to as an eyeglass-type terminal) to be worn on the face portion (head portion), for example, is worn so as to cover eyes of the surgeon (observer) and displays the picked-up images supplied from the control unit 11. For example, the FMD 15 that employs a see-through optical system can display various kinds of information without an external field of view being blocked. As such an FMD 15, an eyeglass-type display apparatus constituted so that a virtual display region is disposed in part of a field of view of a wearer may be employed. Note that the virtual display region can be obtained by, for example, displaying an information image generated by a display controller (not illustrated) at a display unit disposed in part of a region of the field of view. The FMD 15 that employs the see-through optical system can provide a field of view obtained through lenses of the eyeglasses and a field of view obtained in the virtual display region to the wearer. A user can visually confirm an external condition and at the same time, can acquire various kinds of information by visually confirming the information image displayed at the display unit in a virtual display field of view.

While FIG. 1 illustrates an example where the control unit 11 and the condition determination circuit 20 are constituted separately from the FMD 15, it is also possible to employ a configuration where the control unit 11 and the condition determination circuit 20 are incorporated into the FMD 15.

A camera 15a constituted with an image pickup device including an image pickup element such as a CCD and a CMOS sensor is attached to the FMD 15. The camera 15a can, for example, pick up an image of a range equivalent to a field of view range of the wearer who wears the camera 15a. By fixing the camera 15a to the FMD 15, the image pickup range of the camera 15a changes in accordance with movement of the head portion of the wearer. The picked-up image by the camera 15a is supplied to the condition determination circuit 20. A line-of-sight detection sensor 15c and a voice microphone 15d are also attached to the FMD 15.

In other words, if a determination unit (which may be incorporated into the FMD 15 or provided outside of the FMD 15) is provided, which determines, in work on an object within a space, which one of a first picked-up image by a first image pickup unit disposed at a first predetermined position within the space and a second picked-up image by a second image pickup unit disposed at a second predetermined position different from the first predetermined position within the space is appropriate for observation of the work on the object and outputs a determination result, the control unit (which may also be incorporated into the FMD 15 or may be provided outside of the FMD 15) can control a head mounted type display apparatus (FMD 15) worn by the surgeon so as to perform display using at least one of the first picked-up image or the second picked-up image based on the determination result. In a case where a control unit, and the like, are provided within the FMD, a simple system in which the image pickup units and the FMD coordinate with each other in a wired or wireless manner, can be provided.

Further, an acceleration sensor 15*b* is also attached to the FMD 15. The acceleration sensor 15*b* can detect movement of the FMD 15 and can supply the detection result to the condition determination circuit 20.

The condition determination circuit 20 as the determination unit may be constituted with a processor using a CPU, an FPGA, or the like, may operate in accordance with a program stored in a memory (not illustrated) to control respective units, or may implement part or all of functions with a hardware electronic circuit. FIG. 1 illustrates functions to be implemented by the condition determination circuit 20 with functional blocks.

The condition determination circuit 20 not only receives the first and the second picked-up images from the control unit 11 but also includes a communication circuit (not illustrated), so that the condition determination circuit 20 can receive the picked-up images from the external camera 14, the camera 15*a* and the camera 13*a* provided at the display unit 13 and an output of the acceleration sensor 15*b* in a wired or wireless manner. Further, the condition determination circuit 20 can receive information stored in the work database 12 directly or by way of the control unit 11.

FIG. 3 is an explanatory diagram for explaining a method for condition determination by the condition determination circuit and a view for explaining switching between the main image and the sub image.

If a screen is switched during insertion (work) into the space or while the surgeon is concentrating on work of procedure on an object within the space (performing work while confirming work process), there is a possibility that the surgeon may lose sight of information that becomes a foothold during work or a target, and thus, switching from the main image is not preferable. In other words, a condition in which the surgeon performs work with help from the main image is assumed. The work process assumes a predetermined time width in which an apparatus or an instrument moves within the space and an aspect of the movement within the space and change of a positional relationship between the object and the instrument are confirmed.

The screen may be switched during a period other than a period while the surgeon confirms the work process in a concentrated manner. Control of switching among a plurality of images is performed based on such idea, and thus, the present application can be regarded as an invention of a display control apparatus including a determination unit configured to, in work on an object within a space, output a determination result as to which of images by a plurality of image pickup units disposed at a plurality of predetermined positions within the space is appropriate for observation of the work on the object in accordance with a positional relationship between a posture and an observation direction of an operator who performs the work and a portion on which work is to be performed when the work is performed, and a control unit configured to control display using at least one of the plurality of image pickup units based on the determination result of the determination unit, and a control unit configured to, in work on an object within a space, control switching of display using at least one of images by a plurality of image pickup units disposed at a plurality of predetermined positions within the space, includes a determination unit configured to, in a case where an apparatus or an instrument moves within the space, output a determination result assuming a time width for confirming an aspect of movement within the space or a time width for confirming change in a positional relationship of a treatment instrument with respect to the object, and a control unit configured to control switching of display using at least one of the plurality of image pickup units based on the determination result of the determination unit.

The picked-up image from the external camera 14 is inputted to a camera image determination unit 22. The camera image determination unit 22 determines a posture and an observation direction of the surgeon (observer) or a condition and operation in which the surgeon inserts the treatment instrument from the picked-up image from the external camera 14 and provides the determination result to the condition determination unit 21. For example, there can be a case where the surgeon moves the head portion to look into a portion that is not displayed to perform confirmation work, while movement of the head portion is relatively small during basic work. The camera image determination unit 22 may determine such a posture of the surgeon during basic work as a basic posture and may determine a posture during confirmation work as a confirmation posture. Further, the camera image determination unit 22 may determine work in which the surgeon inserts the treatment instrument into the body cavity or moves the treatment instrument a lot, as the basic work and may determine work in which the surgeon minutely moves the treatment instrument or operation of opening and closing the treatment instrument as the confirmation work.

For example, the camera image determination unit 22 may detect the surgeon (observer) as a subject through image recognition processing performed on the picked-up image from the external camera 14 and may determine a posture or operation by comparing, on similarity, the posture or the operation with characteristics of the basic posture or basic operation and characteristics of the confirmation posture or confirmation operation stored in the work database 12.

The condition determination unit 21 determines that display in the first display mode in which only the main image is displayed is appropriate from description in a field of the external camera in FIG. 3 in a case where a determination result indicating that the surgeon takes a basic posture or performs basic operation is obtained by the camera image determination unit 22 and outputs the determination result to the control unit 11. Further, the condition determination unit 21 determines that display in the second display mode in which the sub image is displayed is appropriate in a case where a determination result indicating that the surgeon takes a confirmation posture or performs confirmation operation is obtained by the camera image determination unit 22 and outputs the determination result to the control unit 11.

The picked-up image from the camera 15A is provided to an FMD position determination unit 23. The FMD position determination unit 23 can determine whether the surgeon is performing basic work or confirmation work using the picked-up image from the camera 15*a*. In a case where the surgeon takes a basic posture, movement of the FMD 15 is relatively small, and it can be considered that movement of the whole picked-up image from the camera 15a is relatively small. In contrast, in a case where the surgeon takes a confirmation posture, movement of the FMD 15 becomes relatively large by motion of the surgeon for confirmation, and it can be considered that movement of the whole picked-up image from the camera 15a becomes relatively large. The camera image determination unit 22 can determine whether the FMD 15 moves little from a fixed position, that is, the surgeon performs basic work, or the FMD 15 moves in association with motion for confirmation, that is, the surgeon performs confirmation work, for example, by detecting movement of the picked-up image from the camera 15a. The camera image determination unit 22 also outputs the determination result to the control unit 11.

As indicated in a field of the FMD in FIG. 3, the condition determination unit 21 determines that display in the first display mode in which only the main image is displayed is appropriate in a case where a determination result indicating that the FMD 15 is at the fixed position is obtained by the camera image determination unit 22 and determines that display in the second display mode in which the sub image is displayed is appropriate in a case where a determination result indicating that the FMD 15 moves by motion for confirmation is obtained and outputs the determination result to the control unit 11. A line of sight of the surgeon is detected by a line-of-sight detection sensor 15c, and in a case where the line of sight is directed to a confirmation portion, the condition determination unit 21 determines that display in the second display mode is appropriate and outputs the determination result to the control unit 11. In this event, the line of sight direction may be determined based on scene data accumulated in the work database 12.

In a field of the treatment instrument in FIG. 3, an arrow indicates an insertion direction of the treatment instrument 34 and a position of the distal end of the treatment instrument 34, and ellipses indicate positions of the first image pickup unit C1 and the second image pickup unit C2. The first and the second picked-up images from the image pickup units C1 and C2 are provided to a treatment instrument determination unit 24. The treatment instrument determination unit 24 determines whether or not the treatment instrument 34 is moving (is being inserted) to an observation target portion or insertion to the vicinity of the observation target portion is stopped by the first and the second picked-up images. For example, the treatment instrument determination unit 24 can detect an image portion of the treatment instrument 34 by performing image analysis processing on the first and the second picked-up images and can determine an insertion state and a stopped state of the treatment instrument 34. The treatment instrument determination unit 24 determines whether or not the treatment instrument 34 is in the insertion state or a state where the treatment instrument 34 is stopped and is to treat (pinch) the target portion and outputs the determination result to the condition determination unit 21.

Figure 2B:
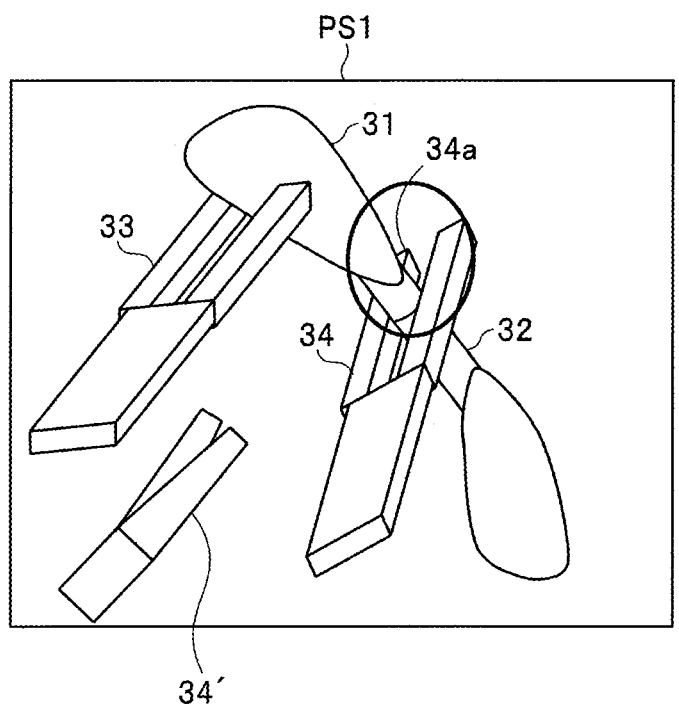
FIG. 2B is an explanatory diagram for explaining an example of determination of an insertion state.

As indicated in the field of the treatment instrument in FIG. 3, the condition determination unit 21 determines that display in the first display mode in which only the main image is displayed is appropriate by a determination result indicating that the treatment instrument 34 is in the insertion state, and the condition determination unit 21 determines that display in the second display mode in which the sub image is displayed is appropriate and outputs the determination result to the control unit 11 if the state of the treatment instrument 34 becomes the stopped state, that is, a state where the treatment instrument 34 is to treat (pinch) the target portion. Further, the treatment instrument determination unit 24 may detect a size of the image of the distal end 34a of the treatment instrument from the first and the second picked-up images and may output the determination result to the condition determination unit 21. In this case, the condition determination unit 21 determines that the treatment instrument 34 is in the insertion state and determines that display in the first display mode in which only the main image is displayed is appropriate in a case where the size of the distal end 34a of the treatment instrument on the image is smaller than a predetermined size, and determines that the treatment instrument 34 is in a state where the treatment instrument 34 is to treat the target portion and determines that display in the second display mode in which the sub image is displayed is appropriate in a case where the size of the distal end 34a of the treatment instrument on the image is larger than the predetermined size and outputs the determination result to the control unit 11. Further, as illustrated in FIG. 2B, in a case where a new treatment instrument 34' appears in a field of view, the treatment instrument determination unit 24 may determine that the treatment instrument 34' is in the insertion state and determine that display in the first display mode in which the main image is displayed is appropriate.

An insertion determination unit 25 determines whether or not the insertion portion 1 is being inserted into the body cavity and outputs the determination result to the condition determination unit 21. For example, the insertion determination unit 25 may determine whether or not the insertion portion 1 is moving, that is, is being inserted from movement of the picked-up image by performing image analysis on at least one picked-up image from the first or the second image pickup unit C1 or C2. The insertion determination unit 25 may determine that the insertion portion 1 is not being inserted and may determine that the target portion is being confirmed in a case where the movement of the whole first or the second picked-up image is relatively small. The insertion determination unit 25 outputs the determination result to the condition determination unit 21. Further, as indicated in a field of an affected area in FIG. 3, the insertion determination unit 25 may compare sizes of a procedure target portion 32a of the lumen 32 on the image between the first and the second picked-up images, detect an image pickup unit closer to the procedure target and may output the result to the condition determination unit 21.

As indicated in a field of an endoscope apparatus in FIG. 3, the condition determination unit 21 determines that display in the first display mode in which only the main image is displayed is appropriate by a determination result indicating that the insertion portion 1 is being inserted and, the condition determination unit 21 determines that display in the second display mode in which the sub image is displayed is appropriate and outputs the determination result to the control unit 11 if the state becomes the stopped state, that is, insertion operation of the insertion portion 1 ends and the state becomes a state where the target portion is being confirmed.

An image pickup range determination unit 26 receives the first and the second picked-up images from the first and the second image pickup units C1 and C2 and determines whether a stage is a stage where the insertion portion 1 is exploring the observation target portion such as an affected area, or a state in which procedure on the affected area is to be started. For example, the image pickup range determination unit 26 acquires information on characteristics regarding the observation target portion such as the affected area corresponding to current procedure from the work database 12 and specifies the observation target portion from the first and the second picked-up images by determining whether or not characteristics of each portion within the image pickup range match the characteristics of the observation target portion through image analysis on the first and the second picked-up images. The image pickup range determination unit 26 may determine that the observation target portion is being explored in a case where there is no observation target portion within the first and the second picked-up images or in a case where the observation target portion makes a relatively big movement within the first and the second picked-up images. Further, the image pickup range determination unit 26 may determine that exploration ends and the stage reaches a stage where procedure is to be started in a case where the observation target portion moves little in the first and the second picked-up images. The image pickup range determination unit 26 outputs the determination result to the condition determination unit 21.

As indicated in the field of the affected area in FIG. 3, the condition determination unit 21 determines that display in the first display mode in which only the main image is displayed is appropriate by a determination result indicating that exploration is being performed and determines that display in the second display mode in which the sub image is displayed is appropriate by a determination result indicating that the procedure is to be started and outputs the determination result to the control unit 11. Note that as the determination result of the condition determination unit 21, determination results displayed in various patterns including a case where only the first or the second display mode is displayed, a case where one of the first and the second display modes is displayed larger and the other is displayed smaller, and a case where the first and the second display modes are displayed in the same size at the same time, may be output to the control unit 11.

Note that the condition determination circuit 20 may perform both determination as to whether the main image is appropriate and determination as to whether the sub image is appropriate or may perform one of determination as to whether the image is appropriate for confirmation of work and determination as to whether the image is not appropriate far confirmation of work for one of the main image and the sub image.

In this manner, the condition determination circuit 20 determines a scene in which display is preferably performed in the second display mode rather than in the first display mode through various kinds of determination. In a case where the present embodiment is applied to a medical apparatus, determination of a scene in which display is preferably performed in the second display mode becomes easier by classifying whether or not a current condition is a confirmation state in accordance with stages of medical action, conditions in the respective stages, and the like. While in the example in FIG. 3, the condition determination circuit 20 determines a scene in which display is preferably performed in the second display mode based on detection results of various kinds of sensors, if the determination is simplified, the mode may be switched between the first display mode and the second display mode in accordance with whether a stage of the procedure is a stage of accessing the target portion or a stage of confirmation work.

In other words, for example, only the main image may be used during access while the endoscope is to be moved to the observation portion, and the sub image may be used when it is desired to confirm the affected area with the sub image during procedure at the observation portion (during confirmation). Further, for example, only the main image may be used while the insertion portion 1 is moving, and if the insertion portion 1 is stopped and procedure by the treatment instrument 34 is started, display may be performed by utilizing the sub image.

Further, while an example has been described in the above description, where the first and the second picked-up images are subjected to image analysis to determine respective image pickup ranges of the first and the second image pickup units C1 and C2, the image pickup ranges of the first and the second image pickup units C1 and C2 may be estimated from positions of the first image pickup unit C1 and the second image pickup unit C2.

For example, by providing a sensor that confirms the positions of the first image pickup unit C1 and the second image pickup unit C2 at the insertion portion 1, the positions of the first image pickup unit C1 and the second image pickup unit C2 can be determined from a sensor output, and the image pickup ranges can be estimated. Further, a relative positional relationship between the first image pickup unit C1 and the second image pickup unit C2 is determined, and the position of the second image pickup unit C2 can be obtained from the position of the first image pickup unit C1. In a similar manner, information on an image pickup direction and an angle of view of the first image pickup unit C1, and information on an image pickup direction and an angle of view of the second image pickup unit C2 are known, and an image pickup range of the sub image can also be estimated from the main image. By utilizing the estimation result, it is possible to perform determination as to whether or not the sub image is preferably used for a portion to be confirmed, such as the affected area.

Further, the method for determining whether basic work or continuation work is performed is not limited to the above-described method, and various methods can be considered. For example, the determination can be performed using change in a posture of an operator. For example, the condition determination as to whether the wearer performs basic work or confirmation work may be performed by determining whether or not the wearer performs motion for confirmation from an output of the acceleration sensor 15b by utilizing the acceleration sensor 15b of the FMD 15. Further, an image in which a range into which the wearer is gazing is picked up larger or an image in which the range into which the wearer is gazing is picked up closer to a central portion may be determined as an appropriate image by utilizing the line-of-sight detection sensor 15c of the FMD 15 and estimating an image pickup range in which the wearer is gazing from an output of the line-of-sight detection sensor 15c. Still further, an appropriate image may be determined from an instruction voice of the wearer by utilizing the voice microphone 15d of the FMD 15.

Further, the condition determination unit 21 may determine which of the main image and the sub image is appropriate for confirmation work from a positional relationship of the observation target portion with respect to an insertion direction of the insertion portion 1 and may perform determination for switching the mode between the first display mode and the second display mode.

Note that the condition determination unit 24 may output a determination result indicating that the second display mode is appropriate to the control unit 11 only in a case where determination results indicating that the second display mode is appropriate are obtained from all of the determination units 22 to 26. Further, the condition determination unit 21 may output a determination result indicating that the second display mode is appropriate to the control unit 11 every time a determination result indicating that the second display mode is appropriate is obtained from one of the determination units 22 to 26. Still further, the condition determination unit 21 may output a determination result indicating that the second display mode is appropriate to the control unit 11 in a case where determination results indicating that the second display mode is appropriate are obtained from a predetermined number of determination units or a specific determination unit among the determination units 22 to 26, or the condition determination unit 21 may comprehensively determine the determination results of the determination units 22 to 26 and may output a determination result indicating which of the first display mode and the second display mode is appropriate to the control unit 11.

Figure 4:
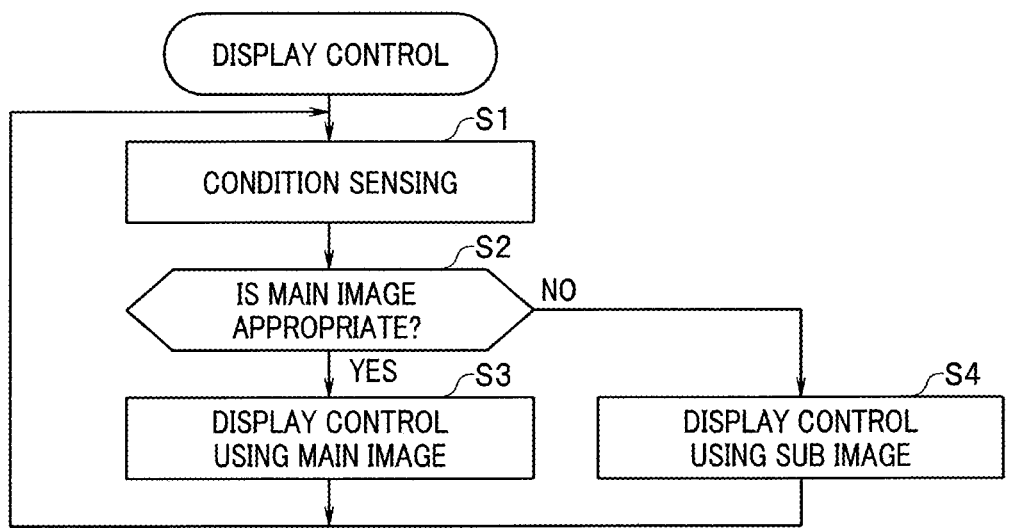
FIG. 4 is a flowchart for explaining control by a control unit 11.

FIG. 4 is a flowchart for explaining control by the control unit 11.

The control unit 11 determines the display mode based on the determination result by the condition determination circuit 20. In step S1 in FIG. 4, the condition determination circuit 20 detects a condition through sensing using outputs of various kinds of sensors and outputs a determination result of the condition to the control unit 11. In step S2, the processing of the control unit 11 branches into step S3 and S4 in accordance with the determination result as to whether or not the condition is appropriate for display of the main image.

In step S2, safety and certainty of work increases by optimal display when an object within a space is accessed while caring collision, or the like, observed or procedure is performed on the object using a tool, an instrument, a treatment instrument, and the like, within the space, and thus, determination is performed to output a determination result in accordance with a posture of the operator who performs the work and a relationship between an observation direction and a position of a portion on which the work is to be performed when the work is performed. The posture can be classified by work or only requires to be determined by a detection result of a positional relationship between a portion to be inserted (or a distal end of an insertion instrument) and the head portion of the operator. Further, in a case where an apparatus or an instrument moves within the space, determination is performed to output a determination result assuming a time width for confirming an aspect of the movement within the space or a time width for confirming change in a positional relationship of the treatment instrument with respect to the object. The time width can be detected from a period during which there is change or no change in each image pickup result, the posture, the observation direction, or the like.

In other words, in a case where a determination result indicating that display in the first display mode in which only the main image is displayed to be appropriate is obtained from the condition determination circuit 20, the control unit 11 provides only the main image to the display unit 13 or the FMD 15 and causes display to be performed in the first display mode in step S3. Further, in a case where a determination result indicating that display in the second display mode in which the sub image is utilized to be appropriate is obtained from the condition determination circuit 20, the control unit 11 provides the sub image to the display unit 13 or the FMD 15 and causes display to be performed in the second display mode in step S4. Note that in the second display mode, only the sub image may be displayed in the whole region of the display screen of the display unit 13 or the FMD 15, or the main image and the sub image may be displayed in the display screen of the display unit 13 or the FMD 15 in a picture-in-picture mode or in a picture-out-picture mode. For example, in the second display mode, the sub image may be displayed on the main image as a sub window. Further, while description has been provided such that only the main image is displayed in the first display mode, in a case where the display region is large, or the like, the sub image may be displayed on the main image as a sub window, and in the second display mode, a main window is replaced with a sub window, that is, the main image may be displayed on the sub image as a sub window.

Further, the control unit 11 may determine which of the first display mode and the second display mode should be designated by determining whether or not the condition is a condition in which confirmation work is required in view of procedure, work, or the like, that is currently being performed as well as the determination result of the condition determination circuit 20.

Figure 5:
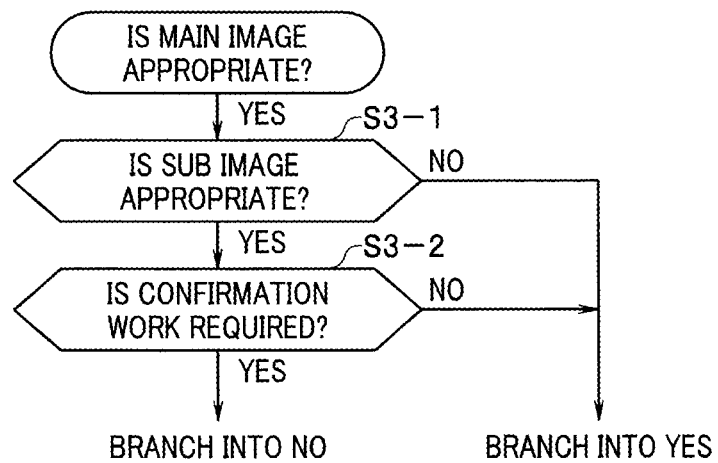
FIG. 5 is a flowchart for explaining display control.
Figure 6:
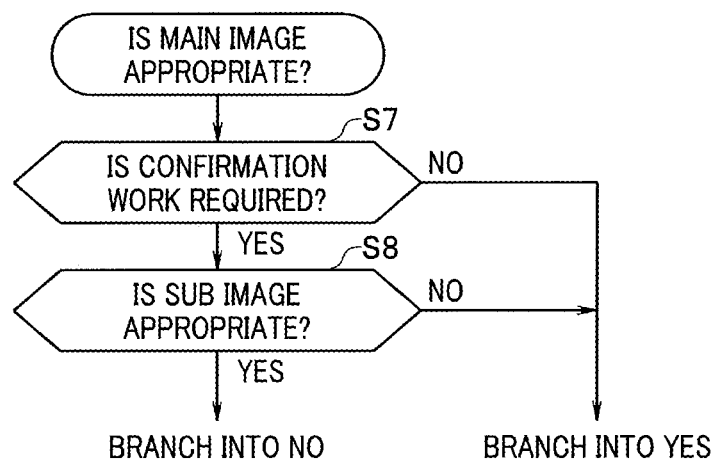
FIG. 6 is a flowchart for explaining display control.

FIG. 5 and FIG. 6 are flowcharts for explaining control in this case. FIG. 5 and FIG. 6 are employed in place of step S2 in FIG. 4.

If the condition determination result is provided from the condition determination circuit 20, the control unit 11 determines whether or not the condition determination result is a determination result indicating that the sub image is appropriate in step S3-1 in FIG. 5. In a case where the condition determination result of the condition determination circuit 20 is a determination result indicating that the main image is appropriate, the processing branches into Yes in step S2 in FIG. 4 from step S3-1, and the control unit 11 performs display control using the main image.

On the other hand, in a case where the condition determination result of the condition determination circuit 20 is a determination result indicating that the sub image is appropriate, the processing transitions to step S3-2 from step S3-1, and the control unit 11 determines whether or not the condition is a condition in which confirmation work is required. The control unit 11 can, for example, determine whether or not the current condition is a condition in which confirmation work is required based on proceeding of the procedure and work process stored in the work database 12 and contents of current procedure (work) that can be determined from input operation, or the like, by the observer. In a case where it is determined that the condition is not the condition in which confirmation work is required, the processing branches into Yes in step S2 in FIG. 4 from step S3-2, and the control unit 11 performs display control using the main image, and in a case where it is determined that the condition is the condition in which confirmation work is required, the processing branches into No in step S2 in FIG. 4 from step S3-2, and the control unit 11 performs display control utilizing the sub image.

If the condition determination circuit 20 outputs a determination result for each determination of all the determination units 22 to 26 to the control unit 11, there is a possibility that the determination result is frequently switched. Also in such a case, the control unit 11 performs display control after determining whether or not confirmation work is required in step S3-2, so that it is possible to prevent display from being difficult to view due to frequent switching of the display mode.

Step S7 and step S8 in FIG. 6 respectively correspond to step S3-2 and step S3-1 in FIG. 5. The flow in FIG. 6 is different from the flow in FIG. 5 only in that determination as to whether or not the condition is a condition in which confirmation work to be required is performed first, and then, display control is performed using the determination result of the condition determination circuit 20, and also in a case where the flow in FIG. 6 is employed, operational effects similar to operational effects obtained in a case where the flow in FIG. 5 is employed can be obtained.

Figure 7:
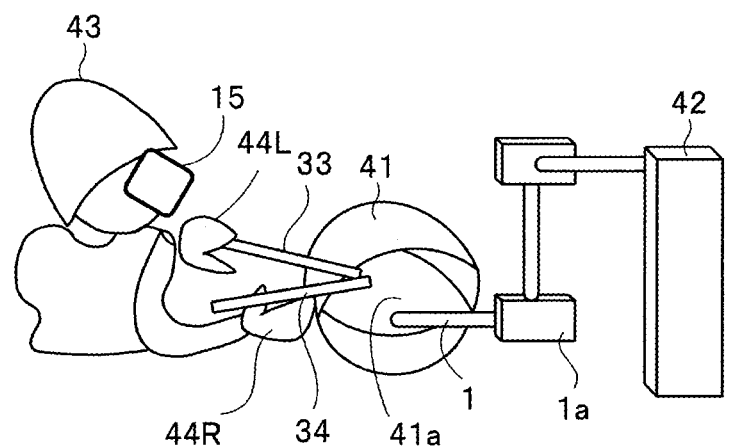
FIG. 7 is an explanatory diagram for explaining an aspect of a surgery.
Figure 8:
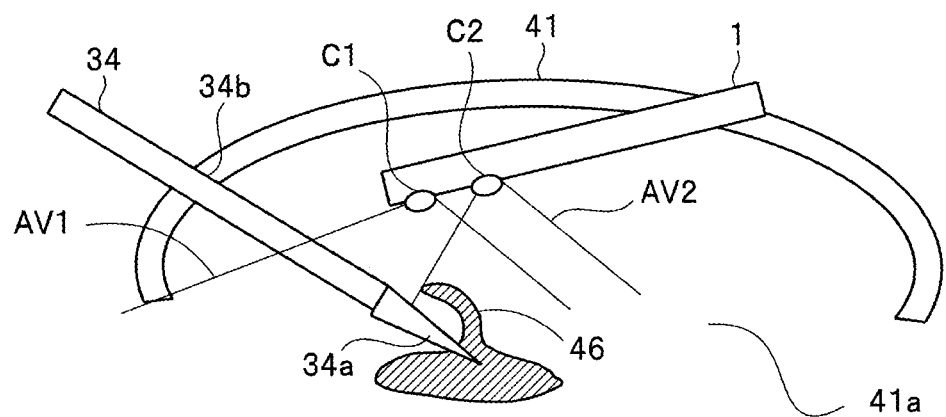
FIG. 8 is an explanatory diagram for explaining an aspect within an abdominal cavity during a surgery.
Figure 9:
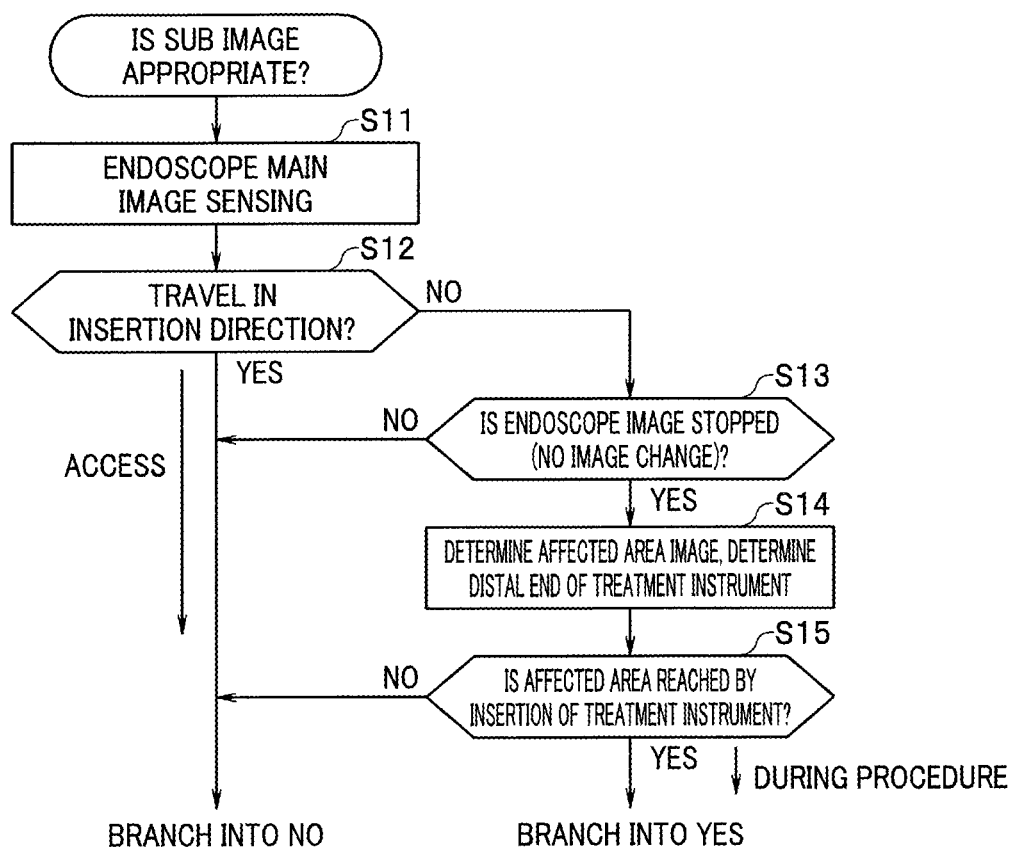
FIG. 9 is a flowchart illustrating display control.
Figure 10:
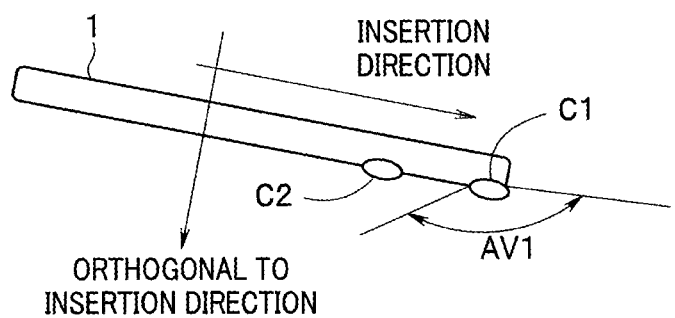
FIG. 10 is an explanatory diagram for explaining display control.
Figure 11:
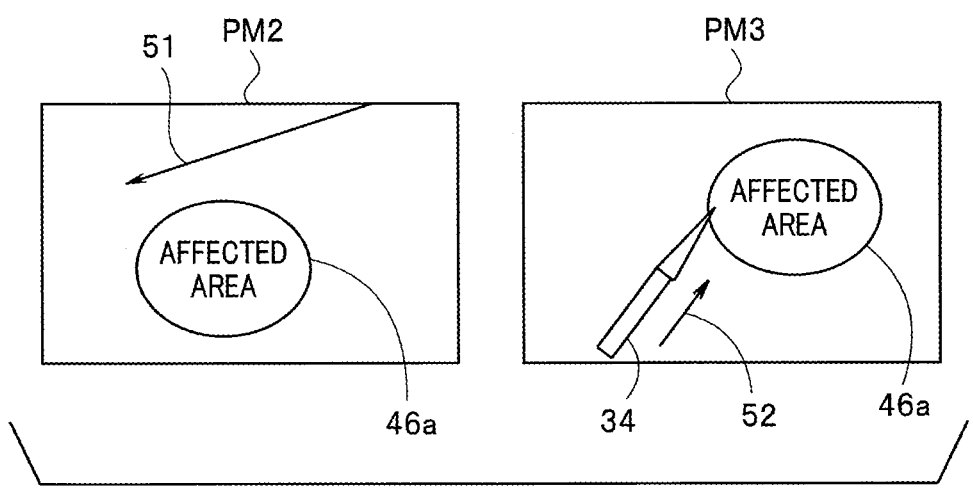
FIG. 11 is an explanatory diagram for explaining display control.

Operation of the embodiment constituted in this manner will be described next with reference to FIG. 7 to FIG. 11. FIG. 7 is an explanatory diagram for explaining an aspect of a surgery, and FIG. 8 is an explanatory diagram for explaining an aspect within an abdominal cavity during the surgery. Further, FIG. 9 is a flowchart illustrating display control, and FIG. 10 and FIG. 11 are explanatory diagrams for explaining display control.

FIG. 7 illustrates an example where the insertion portion 1 of the endoscope 1a is disposed in an abdominal cavity 41a of an abdominal area 41 of a human body. The endoscope 1a, which is supported by a scope holder 42, is inserted to a position at which observation can be performed on an observation target portion within the abdominal cavity 41a, and then, fixed at the position.

A surgeon 43 performs procedure on an affected area within the abdominal cavity 41a while grasping a forceps 33 with the left hand 44L and grasping the treatment instrument 34 with the right hand 44R. The surgeon 43 wears the FMD 15. Note that the FMD 15 can, for example, display the picked-up images from the first image pickup unit C1 and the second image pickup unit C2 provided at the distal end of the insertion portion 1. Note that while the display control apparatus in FIG. 1 is not illustrated in FIG. 7, the picked-up images from the first and the second image pickup units C1 and C2 are supplied to the control unit 11, and the first and the second picked-up images are supplied from the control unit 11 to the FMD 15 in a wired or wireless manner.

FIG. 8 illustrates an aspect of the surgery in the abdominal cavity 41a, and the insertion portion 1 is inserted into the abdominal cavity 41a so that the first image pickup unit C1 and the second image pickup unit C2 are positioned at a position at which an image of the affected area 46 within the abdominal cavity 41a can be picked up. In the state, the surgeon 43 inserts the treatment instrument 34 into the abdominal cavity 41a through a treatment instrument insertion portion 34b and performs procedure at the distal end portion 34a.

In the process of insertion of the insertion portion 1 and procedure by the treatment instrument 34, display in the first display mode or the second display mode is performed on the FMD 15 by utilizing the first and the second picked up images from the first image pickup unit C1 and the second image pickup unit C2. In this case, display control illustrated in any of FIG. 4 to FIG. 6 described above may be employed. For example, description will be provided assuming that display control in FIG. 5 is employed.

FIG. 9 illustrates an example of specific processing in step S3-1 in FIG. 5. In step S11 in FIG. 9, the first picked-up image (main image) from the first image pickup unit C1 is inputted to the condition determination circuit 20. The condition determination circuit 20 determines a traveling direction of the insertion portion 1 through image analysis on the main image (endoscope image sensing). The condition determination circuit 20 determines whether or not the insertion portion 1 is traveling in an insertion direction in step S12. As illustrated in FIG. 10, a longitudinal direction of the insertion portion 1 can be considered as the insertion direction of the insertion portion 1 toward inside of the abdominal cavity 41a. It can be considered that the insertion portion 1 travels in the insertion direction until the distal end portion of the insertion portion 1 reaches the vicinity of the affected area 46.

FIG. 11 illustrates a picked-up image PM2 obtained by the first image pickup unit C1 during insertion and illustrates a picked-up image PM3 obtained by the first image pickup unit C1 when procedure is started. A line 51 in the picked-up image PM2 indicates the traveling direction of the insertion portion 1. The condition determination circuit 20 determines the traveling direction of the insertion portion 1, for example, by change in the picked-up image from the first image pickup unit C1 and outputs the determination result to the control unit 11. Note that the picked-up images PM2 and PM3 include an image 46a of the affected area.

The line 51 in the picked-up image PM2 substantially matches the insertion direction of the insertion portion 1, so that the condition determination circuit 20 obtains a determination result indicating that the traveling direction of the insertion portion 1 substantially matches the insertion direction. In a case where the determination result is obtained, the control unit 11 determines that the insertion portion 1 is in the middle of accessing the affected area 46, and the processing branches into No in step S3-1 in FIG. 5 from step S12. In other words, in this case, the processing in step S3 in FIG. 4 is performed, and the control unit 11 controls the FMD 15 in the first display mode in which only the main image is displayed. The first image pickup unit C1, which has a sufficiently wide angle of view AV1 and can observe a relatively wide range of the abdominal cavity 41a, is effective to be used during insertion into a lumen, exploration of the affected area, and the like. Moreover, only the main image is displayed in the whole area of the screen in the first display mode, which is further advantageous to exploration, and the like.

If the distal end of the insertion portion 1 reaches the vicinity of the affected area 46, the surgeon moves the insertion portion 1 to a position at which the affected area 46 can be easily observed using the first and the second picked-up images. In this case, the insertion portion 1 moves in a direction orthogonal to the insertion direction indicated by an arrow in FIG. 10, and thus, the condition determination circuit 20 determines that the traveling direction does not match the insertion direction from change in the main image, and the processing transitions to step S13.

In step S13, the condition determination circuit 20 determines whether or not the endoscope image is stopped. If the insertion portion 1 reaches the position at which the affected area 46 can be easily observed, the surgeon fixes the insertion portion 1 at the position. As a result, movement of the whole main image is stopped, so that the condition determination circuit 20 determines that the insertion portion 1 is stopped through image analysis of the main image.

Then, the surgeon starts procedure on the affected area 46 with the forceps 33, the treatment instrument 34, and the like. In other words, the surgeon brings the treatment instrument 34 closer to the affected area 46. The picked-up image PM3 in FIG. 11 indicates the picked-up image from the first image pickup unit C1 in this case. The treatment instrument 34 is also included in the picked-up image PM3 in addition to the image 46a of the affected area. Note that in FIG. 11, the traveling direction of the treatment instrument 34 is indicated with an arrow in the picked-up image PM3.

The condition determination circuit 20 recognizes the treatment instrument 34 and determines that the treatment instrument 34 moves toward the affected area 46 by performing image analysis on the main image. Then, the condition determination circuit 20 determines whether or not the distal end of the treatment instrument 34 reaches the affected area 46 in step S15.

If the state becomes a state of the picked-up image PM3, the condition determination circuit 20 determines that the treatment instrument 34 reaches the affected area 46 and procedure is to be started, and the processing branches into Yes in step S3-1 in FIG. 5 from step S15. In other words, in this case, the processing in step S4 in FIG. 4 is performed, and the control unit 11 controls the FMD 15 in the second display mode in which the sub image is utilized for display. As a result, the surgeon can confirm the second picked-up image (sub image) on the display screen of the FMD 15.

As illustrated in FIG. 8, an angle of view AV2 of the second image pickup unit C2 expands toward the distal end of the treatment instrument 34 compared to the angle of view AV1 of the first image pickup unit C1, so that the distal end of the treatment instrument 34 is more likely to be able to be confirmed with the sub image. Thus, by the sub image being displayed on the display screen of the FMD 15, the surgeon can easily confirm from the sub image whether or not the state of the treatment instrument 34 is a state in which procedure can be surely performed on the affected area 46. Further, the first image pickup unit C1 and the second image pickup unit C2 have image pickup ranges that at least partially overlap with each other. By this means, continuity of the first picked-up image and the second picked-up image is secured, which makes it easy for the condition determination circuit 20 to perform condition determination. Further, the same portion can be confirmed from different directions, so that it is possible to reduce a blind area and reliably support operation.

As described above, in the present embodiment, images that are required by the surgeon for surely performing procedure can be switched and displayed in accordance with a condition of the procedure.

Note that while an example has been described in the description of the operation where the mode is switched from the first display mode to the second display mode as a result of it being detected that the insertion portion 1 is stopped and the treatment instrument 34 reaches the affected area 46, as described above, the mode may be switched from the first display mode to the second display mode, for example, by it being detected that the surgeon performs motion for confirmation or the surgeon performs operation for opening and closing the treatment instrument. The display mode only requires to be switched by utilizing various kinds of condition determination described above.

Further, while an example has been described in the determination of insertion and the condition determination in FIG. 9 where the first picked-up image is used, the second picked-up image may be used, or both the first and the second picked-up images may be used, which can similarly apply to the following description. Note that the first image pickup unit C1 and the second image pickup unit C2 have different field of view ranges, and thus, the field of view range which corresponds to a blind area of one image pickup unit can be supplemented by the picked-up image of the other image pickup unit. Thus, by detecting that the surgeon performs motion for confirmation and displaying the first picked-up image in PinP or PoutP in addition to the image that is being displayed, for example, the second picked-up image based on the result, it becomes possible to observe a blind area of the second picked-up image, for example, a side surface of the affected area, so that it is possible to perform procedure more safely.

In this manner, in the present embodiment, the first and the second image pickup units having image pickup ranges different from each other are attached to the insertion portion, and the mode is automatically switched between the first display mode in which display is performed only with the first picked-up image by the first image pickup unit and the second display mode in which display of the second picked-up image by the second image pickup unit is performed, through determination of conditions of a surgery, work, and the like. By this means, the surgeon, and the like, can confirm images necessary for work without performing cumbersome operation.

(Modifications)

Figure 12:
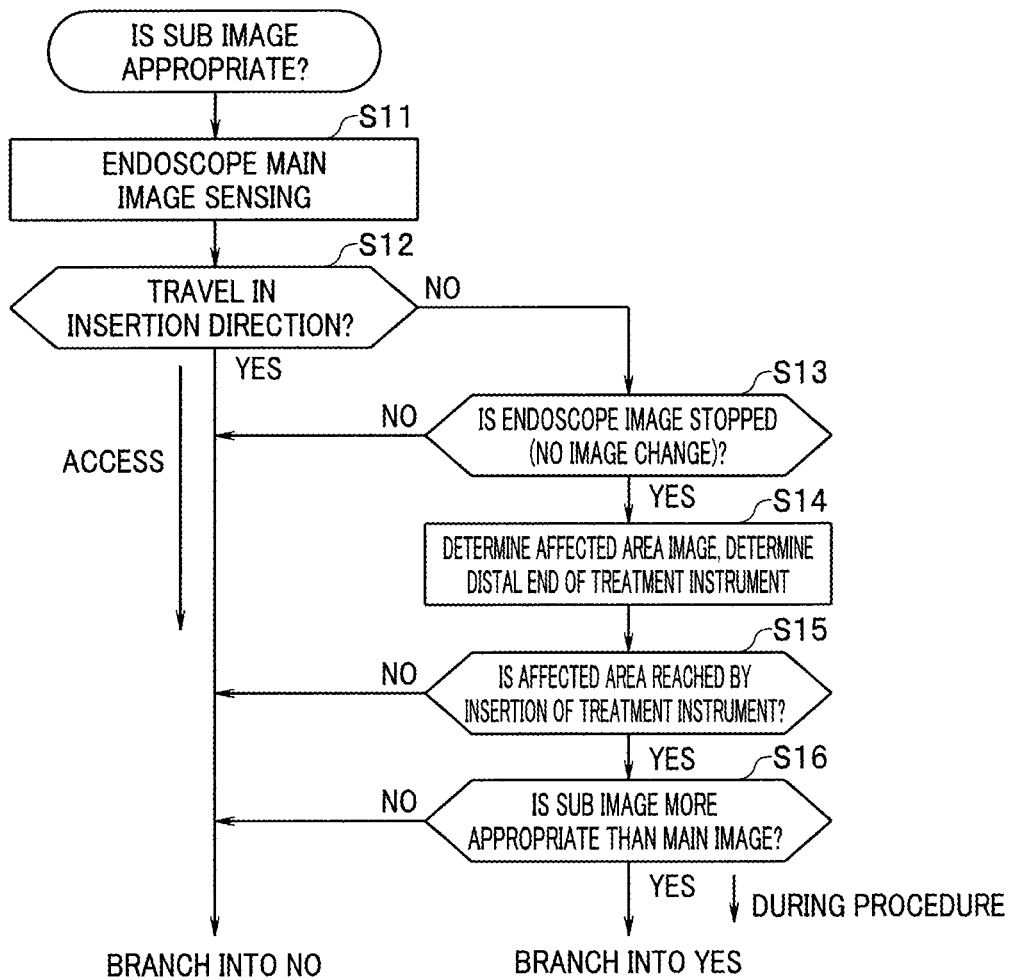
FIG. 12 is a flowchart illustrating a modification.

FIG. 12 is a flowchart illustrating a modification.

In the flowchart in FIG. 9, an example where the mode transitions from the first display mode to the second display mode depending on whether or not the treatment instrument reaches the affected area has been described. In the present modification, an example will be described where after the determination in step S15, transition from the first display mode to the second display mode is determined by comparing the main image and the sub image to determine which of the main image and the sub image is appropriate for the current condition.

For example, it is assumed that characteristics of an image which is considered to be suitable for a positional relationship between the lumen 32 and the distal end portion 34a of the treatment instrument 34 are stored in the work database 12. The condition determination circuit 20 can determine which of the main image and the sub image is appropriate for the current condition by reading out the characteristics from the work database 12 and comparing the readout characteristics with characteristics of the main image and characteristics of the sub image.

Further, for example, the condition determination circuit 20 can determine which of the main image and the sub image is appropriate for the current condition by determining which of the main image and the sub image can surely include the distal end portion 34a from the characteristics of the image of the distal end portion 34a.

In a case where the condition determination circuit 20 determines that the main image is appropriate, the processing branches into No in step S3-1 in FIG. 5 from step S16. In other words, in this case, the processing in step S3 in FIG. 4 is performed, and the control unit 11 controls the FMD 15 in the first display mode in which only the main image is displayed. Further, in a case where the condition determination circuit 20 determines that the sub image is appropriate, the processing branches into Yes in step S3-1 in FIG. 5 from step S15. In other words, in this case, the processing in step S4 in FIG. 4 is performed, and the control unit 11 controls the FMD 15 in the second display mode in which the sub image is utilized for display. By this means, the surgeon can confirm the second picked-up image (sub image) on the display screen of the FMD 15.

In this manner, in the present modification, after it is determined which of the main image and the sub image is appropriate based on the images themselves, it is determined whether or not to transition from the first display mode to the second display mode, so that the surgeon can obtain sufficient information for surely performing work from the displayed image.

Second Embodiment

Figure 13:
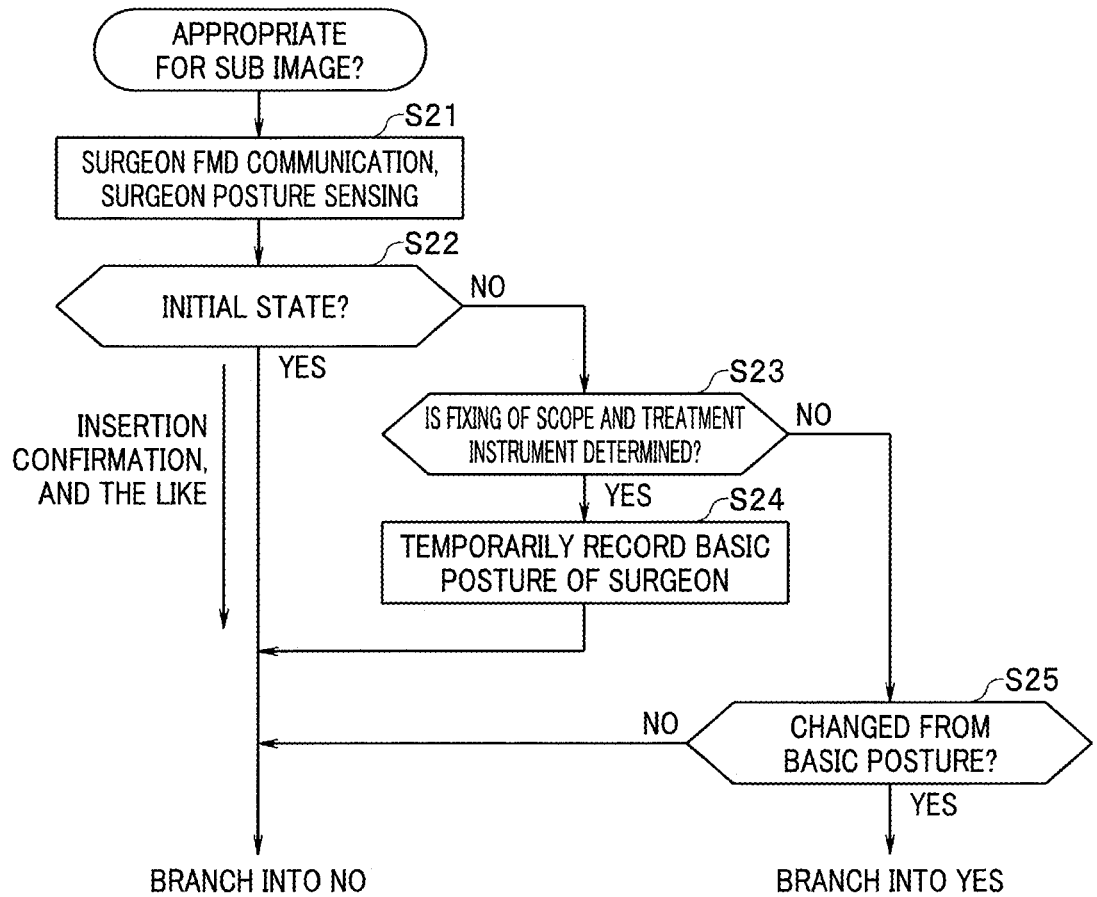
FIG. 13 is a flowchart for explaining a second embodiment of the present invention.
Figure 14:
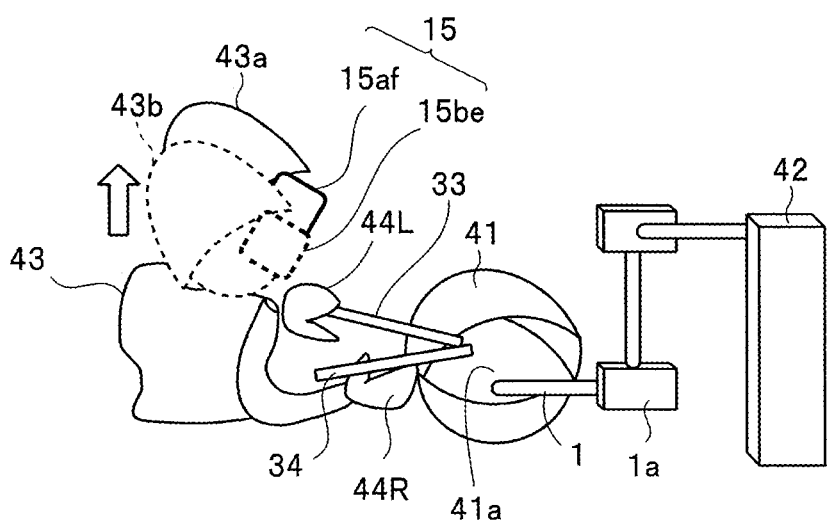
FIG. 14 is an explanatory diagram for explaining the second embodiment.

FIG. 13 and FIG. 14 relate to a second embodiment of the present invention. FIG. 13 is a flowchart for explaining the second embodiment, and FIG. 14 is an explanatory diagram for explaining the second embodiment. A hardware configuration of the present embodiment is similar to the hardware configuration of the first embodiment, and thus, description will be omitted.

In the description of FIG. 9 and FIG. 12 described above, an example has been described where the mode can transition from the first display mode to the second display mode as a result of insertion ending and the treatment instrument reaching the affected area. FIG. 13 illustrates an operation example in a case where the mode can transition from the first display mode to the second display mode by change in a posture of the surgeon. Note that also in the present embodiment, display control of any of FIG. 4 to FIG. 6 described above may be employed. For example, description will be provided assuming that display control in FIG. 5 is employed.

FIG. 13 illustrates an example of specific processing in step S3-1 in FIG. 5. Further, FIG. 14 illustrates an example where the insertion portion 1 of the endoscope 1a is disposed within the abdominal cavity 41a of the abdominal area 41 of the human body in a similar manner to FIG. 7. In step S21 in FIG. 13, the condition determination circuit 20 performs communication with the FMD 15 to detect a posture and an observation direction of the surgeon 43 (posture sensing). For example, the condition determination circuit 20 may detect the posture and the observation direction of the surgeon 43 by analyzing the picked-up image from the camera 15a or may detect the posture and the observation direction of the surgeon 43 by analyzing an output of the acceleration sensor 15b provided at the FMD 15. Alternatively, the condition determination circuit 20 may detect a line of sight of the surgeon 43 by the line-of-sight detection sensor 15c provided at the FMD 15 or may detect voice of the surgeon 43 through the voice microphone 15d provided at the FMD 15 and may analyze an area of concern of the surgeon.

In the flow in FIG. 13, a posture during basic work (hereinafter, referred to as a basic posture) is obtained to determine whether or not it can be determined from the posture and the observation direction of the surgeon 43 that display in the second display mode is desired. Further, the condition determination unit 21 needs to detect change in the posture and the observation direction during procedure using the treatment instrument 34 and does not need to detect change in the posture and the observation direction of the surgeon 43 in a state from insertion of the insertion portion 1 until processing is performed using the treatment instrument 34 (hereinafter, also referred to as an initial state).

In step S22, the condition determination unit 21 determines whether or not the state is the initial state. For example, the condition determination unit 21 determines a state during insertion of the insertion portion 1 as the initial state, and the processing branches into No in step S3-1 in FIG. 5 from step S22. In other words, in this case, the processing in step S3 in FIG. 4 is performed, and the control unit 11 controls the FMD 15 in the first display mode in which only the main image is displayed.

Then, it is assumed that insertion of the insertion portion 1 ends, and the procedure using the treatment instrument 34 is started. For example, as indicated in the picked-up image PM3 in FIG. 11, it is assumed that the treatment instrument 34 reaches the affected area 46a. By this means, the condition determination, unit 21 determines that the current condition is not the initial state, and the processing transitions to step S23.

The condition determination unit 21 determines in step S23 whether or not insertion of the insertion portion 1 ends, the insertion portion 1 is fixed at the position, and the treatment instrument 34 reaches the affected area and is fixed. If insertion of the insertion portion 1 ends, the insertion portion 1 is fixed, and the treatment instrument 34 is also fixed at the position of the affected area, the condition determination unit 21 obtains information on the basic posture of the surgeon 43 and stores the information in a memory (not illustrated) in the next step S24. In a case where the surgeon 43 maintains the basic posture, the condition determination unit 21 causes the processing to branch into No in step S3-1 in FIG. 5 from step S22. In other words, in this case, the processing in step S3 in FIG. 4 is performed, and the control unit 11 controls the FMD 15 in the first display mode in which only the main image is displayed.

In a case where it is difficult to confirm the distal end portion 34a of the treatment instrument 34 with the main image in a condition in which the lumen 32 is to be pinched with the treatment instrument 34 during procedure using the treatment instrument 34, or the like, the surgeon 43, for example, performs motion of looking into the distal end portion 34a of the treatment instrument 34. FIG. 14 illustrates the motion, and the surgeon 43, for example, moves a position of a head portion 43b in a normal posture to a position of a head portion 43a by stretching the neck upward. By the motion, the FMD 15 moves from a position of an FMD 15be to a position of an FMD 15af. The movement is detected by an FMD position determination unit 23 from, for example, the picked-up image of the FMD 15.

By this means, the processing transitions from step S23 to step S25, and the condition determination unit 21 determines whether or not the posture of the surgeon 43 changes from the basic posture. In a case where the surgeon 43 performs motion of looking into the distal end portion 34a, the processing branches into Yes in step S3-1 in FIG. 5 from step S25. In other words, in this case, the processing in step S4 in FIG. 4 is performed, and the control unit 11 controls the FMD 15 in the second display mode in which the sub image is utilized for display. By this means, the surgeon can confirm the second picked-up image (sub image) on the display screen of the FMD 15. Note that instead of the surgeon changing the posture, by the surgeon moving a line of sight within the FMD 15, the FMD position determination unit 23 may detect change in an area of concern of the surgeon and may transmit the determination result to the control unit 11.

In this manner, also in the present embodiment, effects similar to the effects of the first embodiment can be obtained. Note that also in FIG. 13, in a similar manner to FIG. 12, transition from the first display mode to the second display mode may be executed after determination in step S16 in FIG. 12 is performed subsequent to step S25.

Third Embodiment

Figure 15:
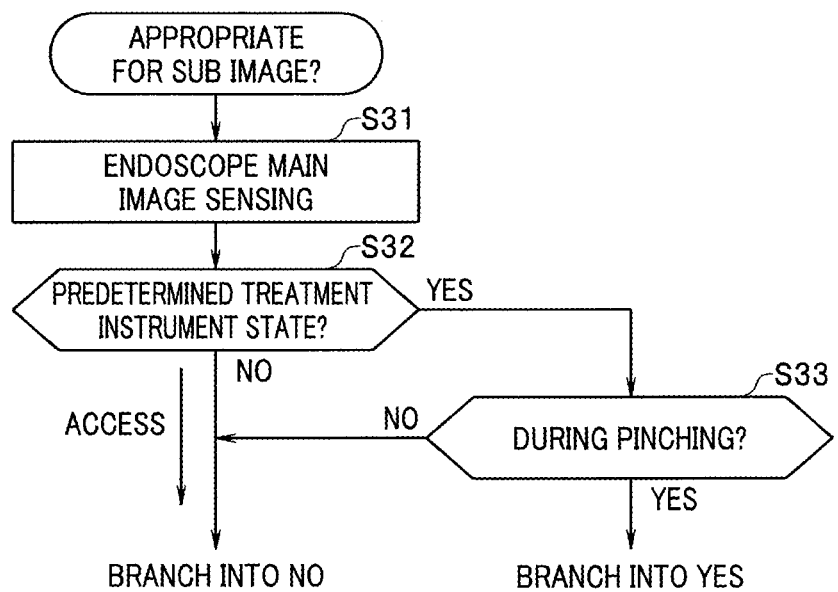
FIG. 15 is a flowchart for explaining a third embodiment of the present invention.

FIG. 15 is a flowchart for explaining a third embodiment of the present invention. A hardware configuration of the present embodiment is similar to the hardware configuration of the first embodiment, and thus, description will be omitted.

In the description of FIG. 9 and FIG. 12 described above, an example has been described where the mode can transition from the first display mode to the second display mode as a result of insertion ending and the treatment instrument reaching the affected area. FIG. 15 illustrates an operation example in a case where the mode can transition from the first display mode to the second display mode in accordance with a state of the treatment instrument corresponding to procedure by the surgeon. Note that also in the present embodiment, display control of any of FIG. 4 to FIG. 6 described above may be employed. For example, description will be provided assuming that display control in FIG. 5 is employed.

FIG. 15 illustrates an example of specific processing in step S3-1 in FIG. 5. In step S31 in FIG. 15, the condition determination circuit 20 performs image analysis on the first picked-up image to detect a predetermined instrument state of the treatment instrument 34 (endoscope main image sensing). In step S32, the condition determination unit 21 determines whether or not the treatment instrument 34 is in a predetermined instrument state. For example, the condition determination unit 21 determines whether or not the treatment instrument 34 is in the predetermined instrument state by reading out information on characteristics indicating the predetermined instrument state of the treatment instrument 34 from the work database 12 and comparing the readout information with image characteristics of the first picked-up image. For example, whether or not the treatment instrument 34 is close to the affected area may be determined as the predetermined instrument state. Alternatively, whether or not the state is an operating state such as opening of the distal end 34a of the treatment instrument, may be determined.

In a case where the condition determination unit 21 determines that the treatment instrument 34 is not in the predetermined instrument state, the processing branches into No in step S3-1 in FIG. 5 from step S32. In other words, in this case, the processing in step S3 in FIG. 4 is performed, and the control unit 11 controls the FMD 15 in the first display mode in which only the main image is displayed.

On the other hand, in a case where the condition determination unit 21 determines that the treatment instrument 34 is in the predetermined instrument state, the processing transitions from step S32 to step S33, and it is determined whether or not pinching is being performed. For example, there is a case where the surgeon performs procedure of only pushing the affected area with the distal end portion 34a of the treatment instrument 34, in which case, the processing branches into No in step S3-1 in FIG. 5 from step S33. In other words, in this case, the processing in step S3 in FIG. 4 is performed, and the control unit 11 continues control of the FMD 15 in the first display mode in which only the main image is displayed.

It is assumed that the surgeon then performs procedure of pinching the lumen 32 with the treatment instrument 34. In this case, the condition determination unit 21, for example, reads out information on image characteristics in a case where the treatment instrument 34 pinches the lumen 32 and compares the readout image characteristics with characteristics of the first picked-up image obtained through image analysis of the first picked-up image. As a result of the comparison, if the condition determination unit 21 detects pinching procedure, the processing branches into Yes in step S3-1 in FIG. 5 from step S33. In other words, in this case, the processing in step S4 in FIG. 4 is performed, and the control unit 11 controls the FMD 15 in the second display mode in which the sub image is utilized for display. By this means, the surgeon can confirm the second picked-up image (sub image) on the display screen of the FMD 15.

Figure 16:
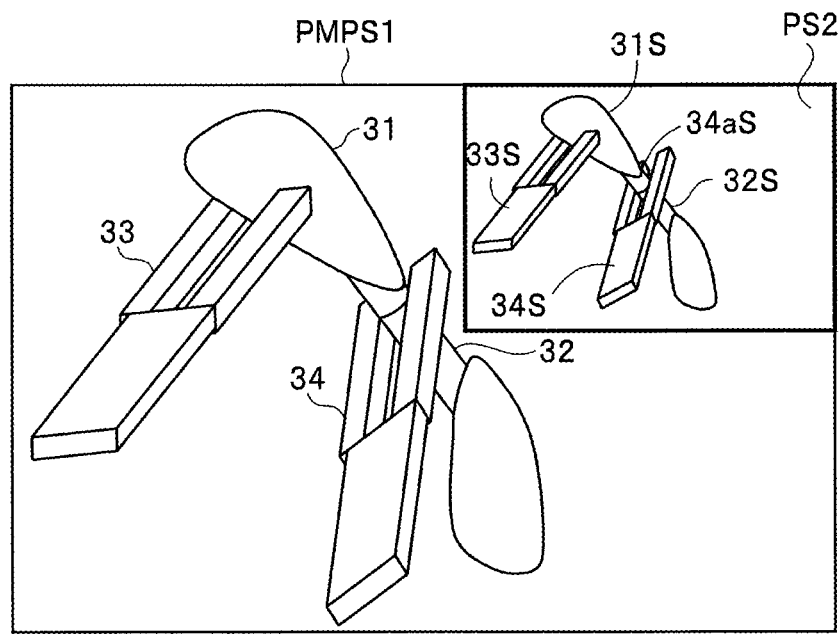
FIG. 16 is an explanatory diagram illustrating a display example of the second display mode.

FIG. 16 is an explanatory diagram illustrating a display example of the second display mode in this case. FIG. 16 illustrates a display image PMPS1 in the second display mode. The display image PMPS1 is displayed at substantially the center of the screen in a similar manner to the main image PM1 in FIG. 2A, and a small image PS2 corresponding to the sub image PS1 in FIG. 2A is displayed in an upper right part of the screen.

The small image PS2 includes images of an organ 31S, a lumen 32S, a forceps 33S and a treatment instrument 34S corresponding to the organ 31, the lumen 32, the forceps 33 and the treatment instrument 34 in the sub image PS1 in FIG. 2A. Further, the small image PS2 includes an image of a distal end portion 34aS of the treatment instrument 34S.

The surgeon can confirm a state where the distal end portion 34a of the treatment instrument 34 surely pinches the lumen 32 by confirming display of the small image PS2.

Note that while in the description of FIG. 15, a condition in which the treatment instrument 34 pinches the lumen 32 is detected as a condition for transition from the first display mode to the second display mode, the condition can be set as appropriate in accordance with a type of work, or the like.

In this manner, also in the present embodiment, effects similar to the effects of the first embodiment can be obtained. Note that also in FIG. 15, in a similar manner to FIG. 12, the mode may transition from the first display mode to the second display mode after determination in step S16 in FIG. 12 is performed subsequent to step S33.

Fourth Embodiment

Figure 17:
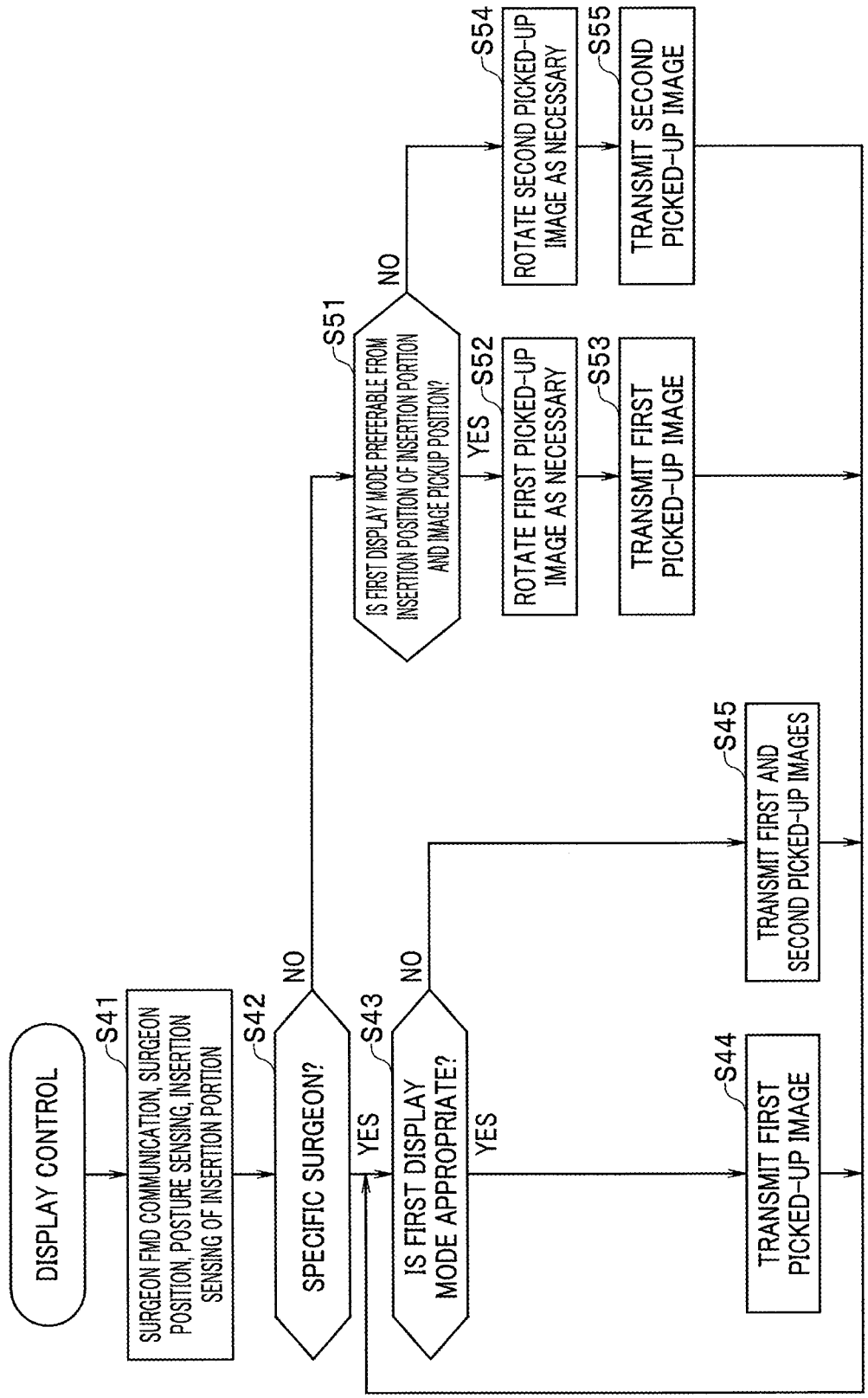
FIG. 17 is a flowchart for explaining a fourth embodiment of the present invention.

FIG. 17 is a flowchart for explaining a fourth embodiment of the present invention. A hardware configuration of the present embodiment is similar to the hardware configuration of the first embodiment, and thus, description will be omitted.

Figure 18:
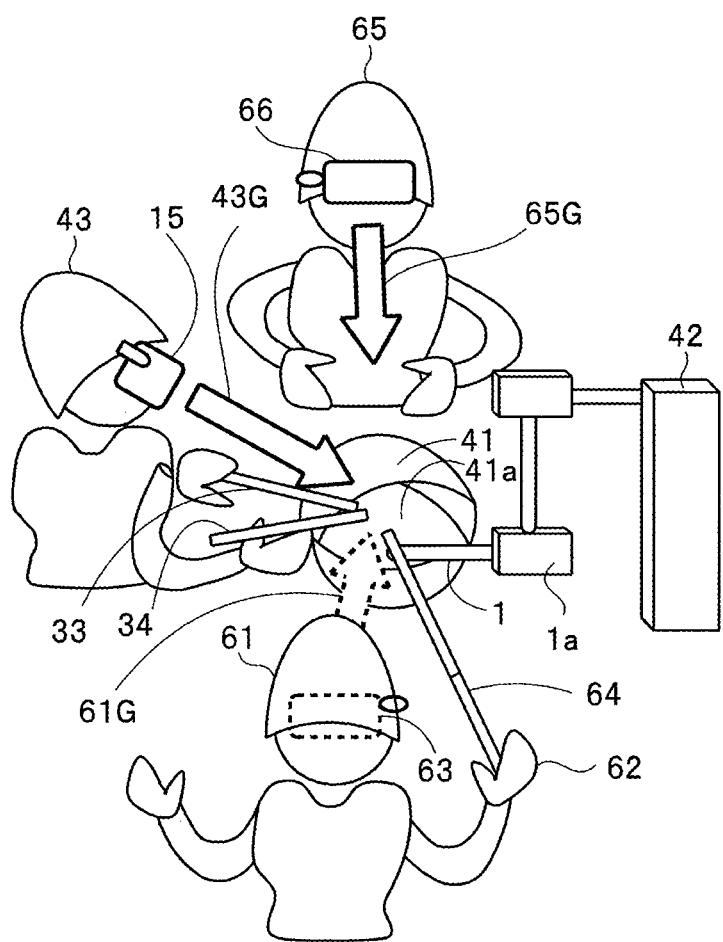
FIG. 18 is an explanatory diagram illustrating on aspect of work by a plurality of surgeons.

While in the above description, the first display mode and the second display mode have been described as modes in which display is performed on the display screen of the display unit 13 or the FMD 15, in a case where there are a large number of surgeons, display may be performed on a plurality of monitors or a plurality of FMDs. The present embodiment supports the case. FIG. 18 is an explanatory diagram illustrating an aspect of work by a plurality of surgeons. FIG. 19 is an explanatory diagram for explaining display on a plurality of monitors or FMDs.

FIG. 18 illustrates an example where the insertion portion 1 of the endoscope 1a is disposed in the abdominal cavity 41a of the abdominal area 41 of the lumen body in a similar manner to FIG. 7. As illustrated in FIG. 18, three surgeons 43, 61 and 65 perform procedure on the patient. The surgeon 43 tries to perform procedure on the affected area of the abdominal cavity 41a while grasping the forceps 33 and the treatment instrument 34, and the surgeon 61 tries to perform procedure on the abdominal cavity 41a while grasping the treatment instrument 64 with the right hand 62. The surgeons 43, 61 and 65 respectively wear FMDs 15, 63 and 66. The FMDs 63 and 66 have configurations similar to the configuration of the FMD 15, and cameras may be attached. Display of the FMDs 63 and 66 is controlled by the control unit 11 in a similar manner to the FMD 15. Further, the FMDs 63 and 66 can perform communication with the condition determination circuit 20 and can supply the picked-up images from the cameras of the FMD 63 and FMD 66 to the condition determination circuit 20. Still further, an acceleration sensor, a position sensor, and the like, may be provided at the FMDs 63 and 66 in a similar manner to the FMD 15, and the detection results may be able to be outputted to the condition determination circuit 20.

In a case where a see-through optical system is employed in the FMDs 15, 63 and 66, the surgeons 43, 61 and 65 can respectively obtain fields of view through display screens of the FMDs 15, 63 and 66. In other words, the surgeons 43, 61 and 65 can capture the abdominal cavity 41*a* beyond respective lines of sight 43G, 61G and 65G and can observe the affected area, the treatment instrument 34, and the like, with the naked eyes.

In step S41 in FIG. 17, the condition determination circuit 20 performs communication with the FMDs 15, 63 and 66 to detect (performs sensing of) the positions, the postures and the observation directions of the surgeons 43, 61 and 65. For example, the condition determination circuit 20 may detect the positions, the postures and the observation directions of the surgeons 43, 61 and 65 by analyzing the picked-up images from the FMDs 15, 63 and 66 and may detect the positions, the postures and the observation directions of the surgeons 43, 61 and 65 by analyzing outputs of acceleration sensors, and the like, provided at the FMDs 15, 63 and 66. Further, the condition determination circuit 20 detects insertion of (performs insertion sensing of) the insertion portion 1.

In step S42, the condition determination unit 21 of the condition determination circuit 20 determines whether or not control is display control on the FMD 15 worn by a specific surgeon (surgeon 43) who performs procedure on the affected area. In a case where display control on the FMD 15 worn by the surgeon 43 is performed, the condition determination unit 21 performs condition determination in the respective embodiments described above to determine which of the first display mode and the second display mode is appropriate and outputs the determination result to the control unit 11.

In a case where a determination result indicating that the first display mode is appropriate is obtained, the control unit 11 transmits the first picked-up image to the FMD 15. Further, in a case where a determination result indicating that the second display mode is appropriate is obtained, the control unit 11 performs display control using the second picked-up image. For example, the control unit 11 transmits a synthesized image based on the first picked-up image and the second picked-up image to the FMD 15.

FIG. 19 illustrates a display example of display regions of the FMDs 15, 63 and 66 and the display unit 13. A main image PM3 and a sub image PS3 are displayed as two screens in the display region 15IS of the FMD 15 as a display example in a case where the second display mode is designated.

On the other hand, in a case where display control on the FMDs 63 and 66 worn by the surgeons 61 and 65 other than the surgeon 43 is performed, the lines of sight 61G and 65G toward the treatment instrument 34, the affected area, and the like, are different from the line of sight 43G, and thus, the condition determination unit 21 determines which of the first display mode and the second display mode is preferable in accordance with respective positions of the FMDs 63 and 66 and outputs the determination result to the control unit 11 (step S51).

In a case where a determination result indicating that the first display mode is preferable is obtained in step S51, the processing transitions to step S52, and the control unit 11 rotates the first picked-up image as necessary, and then, transmits the rotated first picked-up image to the FMDs 63 and 66 in step S53. Further, in a case where a determination result indicating that the first display mode is not preferable is obtained in step S51, the processing transitions to step S54, and the control unit 11 rotates the second picked-up image as necessary, and then, transmits the rotated second picked-up image to the FMDs 63 and 66 in step S55.

FIG. 19 illustrates an example where the first display mode is set to the FMD 63, and the second display mode is set to the FMD 66. A display region 63IS in FIG. 19 indicates a display region of the FMD 63, and the surgeon 61 can confirm the main image by the FMD 63. An image displayed in the display region 63IS is an image obtained by rotating the main image PM3. Further, a display region 66IS in FIG. 19 indicates a display region of the FMD 66, and the surgeon 65 can confirm the sub image by the FMD 66. An image displayed in the display region 66IS is an image obtained by rotating the sub image PS3.

Note that while FIG. 17 illustrates an example where in a case where a determination result indicating that the first display mode is not preferable is obtained in step S51, only the second picked-up image is displayed, the second display mode may be set so as to perform display including the first and the second picked-up images. A display region 13IS in FIG. 19 indicates display in the display region of the display unit 13 in this case, and a synthesized image of the main image and the sub image is displayed in the display region 13IS.

In this manner, in the present embodiment, effects similar to the effects in the above-described embodiments can be obtained, and each surgeon can confirm an optimal image corresponding to his/her line of sight.

Fifth Embodiment

Figure 20:
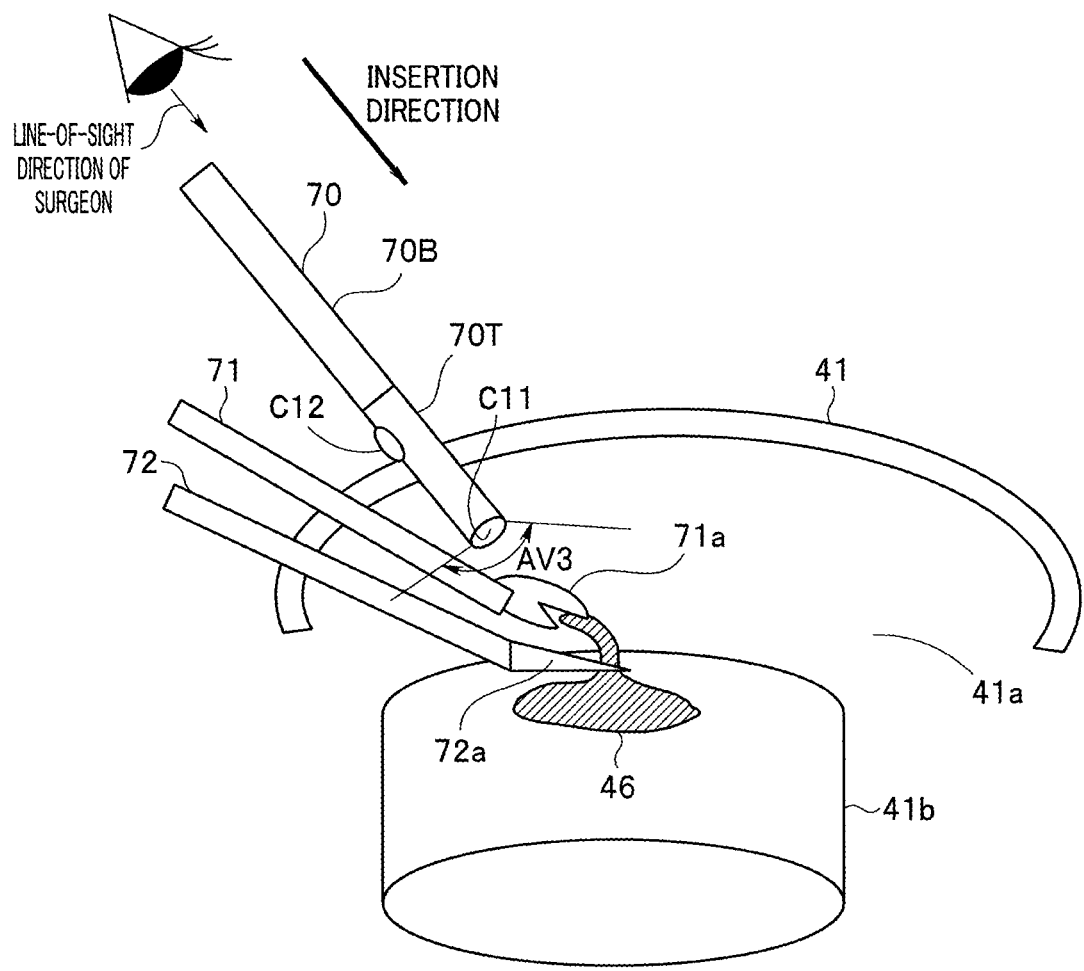
FIG. 20 is an explanatory diagram illustrating a fifth embodiment of the present invention.
Figure 21:
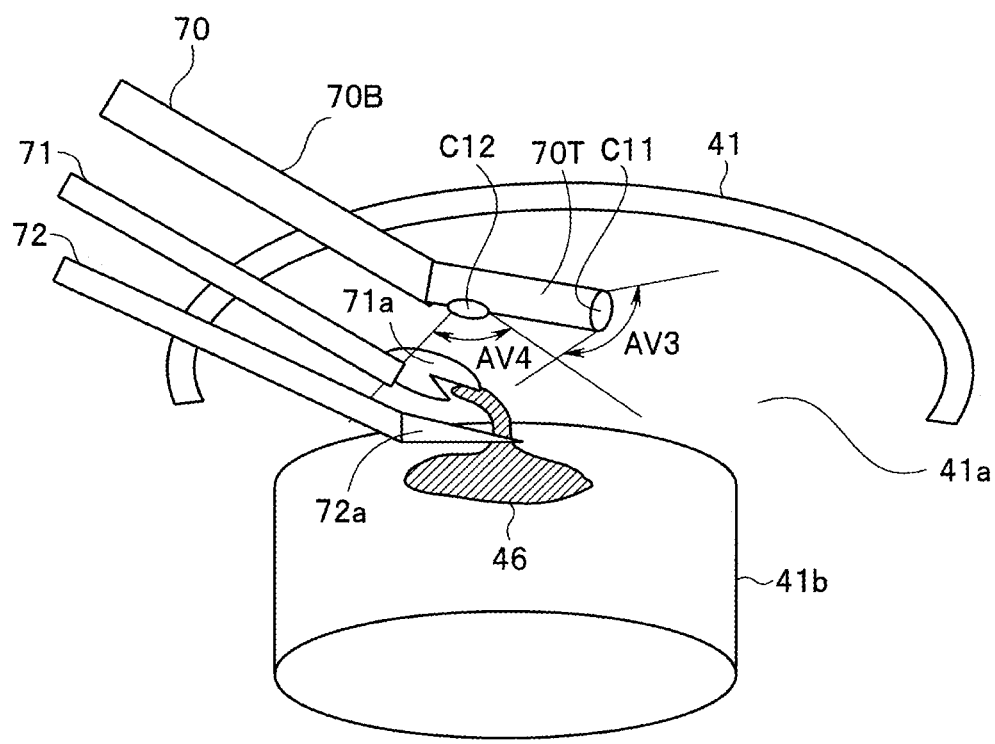
FIG. 21 is an explanatory diagram illustrating the fifth embodiment of the present invention.

FIG. 20 and FIG. 21 are explanatory diagrams illustrating a fifth embodiment of the present invention.

In the present embodiment, an endoscope system having a configuration of an insertion portion of an endoscope different from the configuration in the above-described embodiments is applied. In other words, the present embodiment is different from the above-described embodiments in that in place of the insertion portion 1 in FIG. 1, an insertion portion 70 illustrated in FIG. 20 and FIG. 21 is employed. Note that a configuration of the display control apparatus is similar to the configuration in FIG. 1.

This example enables, in work on an object (affected area) within a space (body cavity), secure and safe processing and work while confirming whether or not collision with body tissues, and the like, within the space occurs, avoiding collision and identifying the object using the first picked-up image by the first image pickup unit disposed at a first predetermined position within the space and the second picked-up image by the second image pickup unit disposed at a second predetermined position different from the first predetermined position within the space, which is a feature of the present application. Portions to be confirmed during insertion and procedure are optimized by switching a main image pickup unit between during insertion work and during confirmation of procedure.

In other words, the image pickup unit provided at the distal end is appropriate for image pickup to confirm that there is nothing around the distal end (portion provided at the head in the insertion direction and entering a deep portion first) during insertion. Thus, also in a case where a member 70T that constitutes the distal end portion proceeds while changing a direction within the body cavity as in FIG. 21, it is possible to safely perform insertion work of moving within the body cavity while confirming that the distal end portion does not contact body tissues. Further, in a case where the surgeon faces the body of the patient as in the drawing and inserts an instrument toward the affected area, the insertion direction during insertion is often a direction in which the surgeon views, because the surgeon can easily perform work with virtual image of looking into the body cavity, can stably perform insertion using the body of the surgeon as a point of support, and can easily perform precise movement by using the both hands as necessary, so that the surgeon can easily perform control while intuitively confirming the space using the picked-up image as an extension of the body of the surgeon with a sense of immersion and concentration. That means, concerning insertion, a design in which the image pickup unit is provided at the distal end of the insertion portion provides extremely accurate workability. In other words, one of the above-described first and second image pickup units is an image pickup unit provided for confirming spatial change in the insertion direction while an insertion member (such as an endoscope) is inserted into the space. The image pickup unit does not have to be physically provided at the distal end and only requires to enable viewing of a space in front of and around the distal end as in FIG. 10 and enable confirmation of a relationship between movement of the distal end portion in association with insertion and a movement space.

Further, the surgeon confirms an aspect where a direction of the member 70T is changed and the member 70T is bent, and thus, it is possible to ensure that each portion of the inserted instrument does not collide in view of image information obtained during insertion process as well as confirmation of the distal end. In other words, it is important to recognize a relationship between behavior of the distal end in association with insertion (movement of the distal end) and the space during the insertion work, and thus, a distal end image pickup unit C11 is appropriate to be dealt with as the main image pickup unit. In this event, while a position of a side surface may be confirmed with reference to an image of the image pickup unit C12 other than the distal end image pickup unit, the image pickup unit C12 is positioned as the sub image pickup unit, because the image pickup unit C12 is not located at a position at which information more than the information obtained by the distal end image pickup unit C11 can be obtained concerning movement of the distal end.

Note that disposing the distal end image pickup unit C11 and the image pickup unit C12 other than the distal end image pickup unit without intervening a flexible portion or disposing the distal end image pickup unit C11 and the image pickup unit C12 other than the distal end image pickup unit at the same member that is not bent have an advantage of being capable of easily gasping a positional relationship between the two image pickup units C11 and C12. Thus, by performing insertion while confirming information on the distal end image pickup unit C11, the image pickup unit C12 (side surface image pickup unit) other than the distal end image pickup unit, which also moves in coordination in a positional change direction during insertion, follows a path through which the distal end passes, so that the image pickup unit can enter the space without contact, or the like. However, in a case where directional change as in FIG. 21 occurs in association with insertion, the image pickup unit C12 provided at a side surface portion does not necessarily move in association with movement of the distal end, and thus, in this case, the condition within the space may be grasped with the side surface image pickup unit C12 as appropriate. Basically, even if the direction of the distal end portion changes from a state in FIG. 20 to a state in FIG. 21, if a portion to be inserted into the space such as the body cavity is the same, the distal end portion moves most, and movement of the side surface portion is less than the movement of the distal end portion, and thus, image pickup at the distal end portion can provide a lot of information amount as information of the image.

Further, as in FIG. 21, in a case where the image pickup unit C12 located away from the distal end portion approaches the affected area 46, procedure is performed by utilizing the image pickup unit C12, and the distal end image pickup unit C11 becomes an auxiliary image pickup unit. In other words, although the image pickup unit C11 is the main image pickup unit during insertion, after insertion ends, the insertion portion is stopped at a specific position, and procedure is started, confirmation of safety during insertion, which is an original main purpose of the distal end image pickup unit C11, is achieved, and thus, the image pickup unit C11 starts to function as the sub image pickup unit, because the image pickup unit C11 is not located at a position at which information more than information obtained by the image pickup unit C12 other than the distal end image pickup unit can be obtained concerning procedure on the target portion.

In this event, the side surface image pickup unit C12 other than the distal end image pickup unit, which has been a so-called sub image pickup unit so far, becomes the main image pickup unit and confirms movement of the distal ends of the treatment instruments 71 and 72. In this event, if the procedure is performed, the side surface image pickup unit C12 provides a lot of information on change in the image and appropriately functions as the main image pickup unit. On the other hand, in this event, the image pickup units C11 and C12 have already been disposed at predetermined positions within the space and stopped, there is no change in the image obtained by the distal end image pickup unit C11. However, the distal end image pickup unit C11 can be effectively utilized as an auxiliary image pickup unit. In other words, the image pickup unit C11 has a wide angle of view, and thus, has an advantage of being capable of monitoring the object from other locations during the procedure. In this manner, works within the space can be roughly divided into a work of changing positions of (a plurality of) image pickup units within the space while displaying image pickup results and the other work of preventing creation of a blind area during the positional change in an instrument that enters fields of view of the (plurality of) image pickup units, and this invention of a display control apparatus can support both works.

Thus, also in the present embodiment, a display control apparatus includes a determination unit configured to, in work on an object within a space, determine which one of a first picked-up image by a first image pickup unit disposed at a first predetermined position within the space and a second picked-up image by a second image pickup unit disposed at a second predetermined position different from the first predetermined position within the space is appropriate for observation of the work on the object and output a determination result, and a control unit configured to control display using at least one of the first picked-up image or the second picked-up image based on the determination result of the determination unit.

In other words, also in the present embodiment, an image pickup apparatus and a display control apparatus are provided, in which one of the first and the second image pickup units is an image pickup unit configured to detect change in an image based on the work in work process on the object after an insertion member in which the image pickup units are provided is inserted into the space and after the image pickup units are stopped at specific positions.

In this manner, image display control such as flexible switching of a screen, which is a feature of the embodiment, is achieved so that in work on an object (affected area) within a space (body cavity), the surgeon can surely perform the work while monitoring process of the work using one of a first picked-up image by a first image pickup unit disposed at a first predetermined position within the space and a second picked-up image by a second image pickup unit disposed at a second predetermined position different from the first predetermined position within the space as a main image in some cases and as a sub image in other cases so that the surgeon focuses on a main image optimal for the work.

Thus, the present embodiment includes an invention of switching which image is preferentially set as a main image (which is exclusively watched during work) and which image is set as a sub image (which supplements a blind area in an auxiliary manner) among images by a plurality of image pickup units (while two image pickup units are illustrated in FIG. 20, and the like, there may be more image pickup units) in accordance with a condition. Further, as illustrated in FIG. 3, the present embodiment includes a determination unit configured to determine an image obtained by which image pickup unit among the plurality of image pickup units is appropriate for observation of the work on the object and output the determination result. The determination is performed to implement optimal display during access to the object within the space while caring collision, or the like, observation and procedure using a tool, an instrument, a treatment instrument, or the like, on the object within the space and is performed to increase safety and certainty of the work, and thus, it is only necessary to perform determination to output a determination result in accordance with a positional relationship between the posture and the observation direction of the operator who performs the work and a portion on which the work is to be performed when the work is performed. The posture can be classified in accordance with work or only requires to be determined by detecting a positional relationship between a portion to be inserted (or a distal end of an insertion instrument) and the head portion of the operator.

Further, in a case where a device and an instrument moves within the space, the determination unit of the embodiment performs determination to output a determination result assuming a time width for confirming an aspect of the movement within the space or a time width for confirming change in a positional relationship of a treatment instrument with respect to the object. The time width can be detected from a period during which there is change or no change in each image pickup result, the posture, the observation direction, or the like. The apparatus in the embodiment only requires to include a control unit configured to control display using at least one of the first picked-up image or the second picked-up image based on the determination result of the determination unit.

Also the endoscope employed in the present embodiment includes the insertion portion 70 which is constituted with, for example, a rigid endoscope, and the like, and which is connected to a camera control unit (not illustrated). The insertion portion 70 of the endoscope includes a member 70T of a distal end portion and a proximal end member 70B. The member 70T is provided on the distal end side of the insertion portion 70, and the proximal end member 70B is provided on the proximal end side. The first image pickup unit C11 and the second image pickup unit C12 are disposed at the member 70T. Note that an illumination optical system constituted with a light guide, and the like, a wiring, and the like, that transmit a subject image (picked-up image) are also disposed within the insertion portion 70.

In the present embodiment, as illustrated in FIG. 21, the insertion portion 70 is constituted so as to be able to be bent at a connection portion between the proximal end member 70B and the member 70T. For example, a hinge member, a joint member, or the like, may be used as appropriate at the connection portion between the proximal end member 70B and the member 70T so as to enable control of extension and bending with a spring member, a tow cable, or the like. For example, a manipulator (not illustrated) is provided on the proximal end side of the insertion portion 70, and bending of the member 70T can be operated through operation of the manipulator.

The first image pickup unit C11 and the second image pickup unit C12 are image pickup devices including image pickup elements such as a CCD and a CMOS sensor (not illustrated) and perform photoelectric conversion of an optical image from a subject to acquire picked-up images. The picked-up images are subjected to image processing by the camera control unit connected to the endoscope, and then, are supplied to the control unit 11 (FIG. 1) of the display control apparatus.

The first image pickup unit C11 is disposed at a distal end of the member 70T. The first image pickup unit C11 has, for example, an ultrawide angle of view AV3 and can pick up an image at an extremely wide angle of view in a direction of the distal end of the member 70T. On the other hand, the second image pickup unit C12 is disposed on a side surface on a proximal end side of the member 70T. The second image pickup unit C12 has, for example, a normal angle of view AV4 and can pick up an image in a predetermined field of view on the side surface side of the member 70T.

As illustrated in FIG. 20, during insertion, the insertion portion 70 passes through a trocar (not illustrated) provided at the abdominal area 41 of the patient, or the like, and is inserted into the abdominal cavity 41a. For example, during insertion as illustrated in FIG. 20, the member 70T is extended so as to make the entire shape of the insertion portion 70 a substantially linear shape to facilitate insertion. Further, during insertion, it is preferable to utilize a picked-up image from the first image pickup unit C11 provided at the distal end of the member 70T to confirm the insertion direction.

FIG. 21 illustrates an aspect where part of the affected area 46 is pinched with a distal end portion 71a of the forceps 71 and pulled, and part of the affected area 46 is subjected to predetermined procedure such as, for example, resection with a distal end portion 72a of a treatment instrument 72. During the procedure, as illustrated in FIG. 21, there is a case where the member 70T is bent. As illustrated in FIG. 21, during the procedure, there is a case where the insertion portion 70 is disposed at such a position that the distal end of the member 70T passes through the vicinity of the affected area 46 and a side surface of the member 70T substantially faces the affected area 46. In this case, it is preferable to perform procedure utilizing the picked-up image from the second image pickup unit C12.

In this manner, in the present embodiment, the first image pickup unit C11 is provided at the distal end of the insertion portion 70, and thus, insertion work is preferably performed while referring to the first picked-up image from the first image pickup unit C11 during insertion. Further, during procedure, the second image pickup unit C12 faces the affected area 46, and thus, procedure is preferably performed while referring to the second picked-up image from the second image pickup unit C12. Still further, the first image pickup unit C11 has an ultrawide angle of view AV3 and can pick up an image of a wide range, and thus, may be able to pick up an image of a blind area that cannot be picked up with the second image pickup unit C12, so that the first picked-up image from the first image pickup unit C11 can also be used during procedure in an auxiliary manner. In other words, in the present embodiment, it can be said that the second picked-up image is the main image, and the first picked-up image is the sub image.

Image pickup ranges of the first and the second image pickup units C11 and C12 during insertion and during procedure will be described next with reference to the explanatory diagrams in FIG. 22 and FIG. 23.

Figure 22:
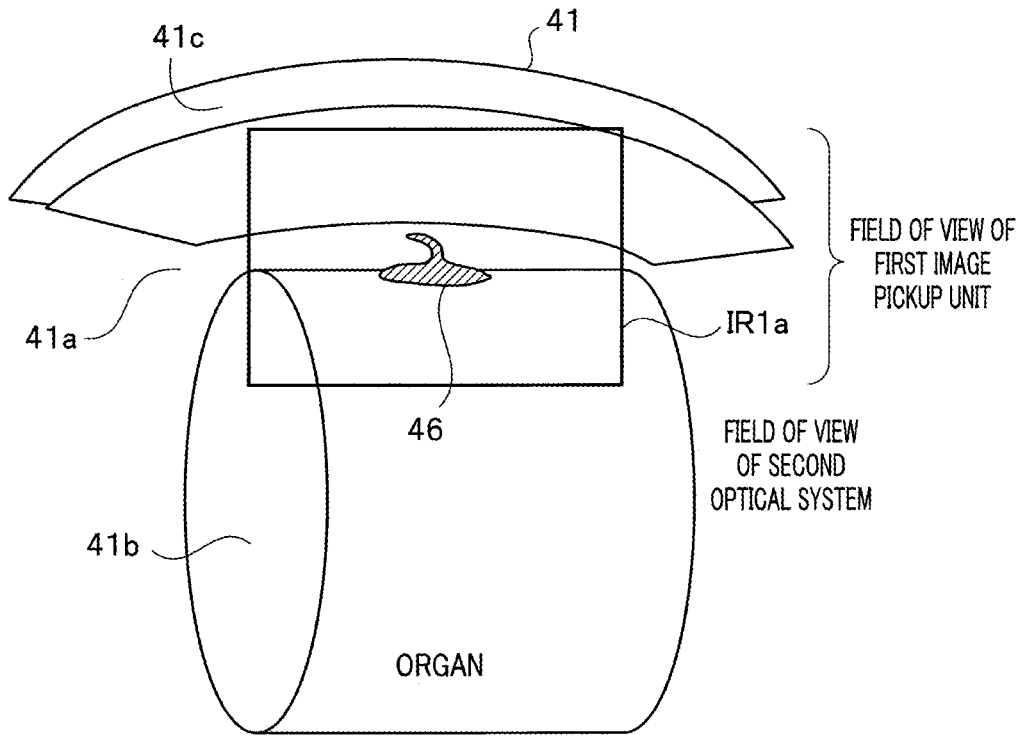
FIG. 22 is an explanatory diagram for explaining an image pickup range during insertion.

FIG. 22 illustrates an image pickup range IR1a by the first image pickup unit C11 during insertion illustrated in FIG. 20. In the example in FIG. 20 and FIG. 22, the insertion portion 70 is inserted toward the abdominal cavity 41a between an abdominal wall 41c and an organ 41b. The insertion portion 70 proceeds in the abdominal cavity 41a, and thus, as illustrated in FIG. 22, an image of a wide image pickup range IR1a including part of the abdominal wall 41c, part of the organ 41b and part of the abdominal cavity 41a is picked up by the first image pickup unit C11 provided at the distal end of the insertion portion 70. The first image pickup unit C11 has an ultrawide angle of view, and the first picked-up image (sub image) is effective for confirmation during insertion.

Figure 23:
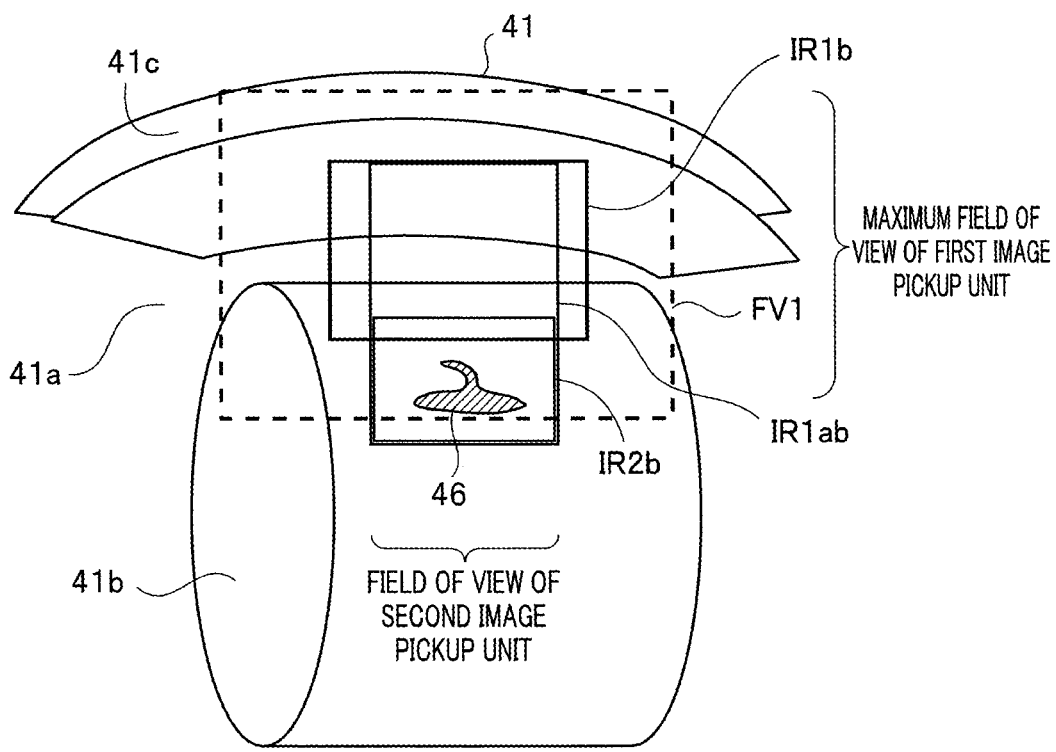
FIG. 23 is an explanatory diagram for explaining an image pickup range during procedure.

FIG. 23 illustrates image pickup ranges of the first and the second image pickup units C11 and C12 during transition from insertion in FIG. 20 to the procedure illustrated in FIG. 21. Note that the example in FIG. 23 illustrates an example where only part of a range among a sufficiently wide field of view range FV1 by the first image pickup unit C11 is used as the image pickup range. An image pickup range IR1b in FIG. 23 indicates an image pickup range of the first image pickup unit C11 at a time point at which the member 70T is bent and the procedure is started as illustrated in FIG. 21. Further, an image pickup range IR2b indicates an image pickup range of the second image pickup unit C12 at a time point at which the member 70T is bent and the procedure is started as illustrated in FIG. 21.

The image pickup range IR2b of the second image pickup unit C12 includes the affected area 46, and thus, the surgeon can confirm an aspect of the affected area 46, the treatment instrument 72, and the like, during the procedure with the second picked-up image (main image). However, there is a case where the distal end portion 72a, or the like, of the treatment instrument 72 is located in a blind area of the second picked up image. Also in this case, the image pickup range IR1b of the first image pickup unit C11 (or the field of view range FV1) is sufficiently wide, and thus, there is a possibility that the blind area of the second picked-up image is picked up by the second image pickup unit C12. Thus, during the procedure, display is performed in the second display mode using the second picked-up image (main image) and the first picked-up image (sub image).

As illustrated in FIG. 20 and FIG. 21, the insertion portion 70 is inserted toward the vicinity of the affected area 46, and the image pickup range IR1b of the first image pickup unit C11 is a region including the affected area 46 before the member 70T is bent, so that the affected area 46 can be confirmed with the sub image. The state becomes a state in FIG. 21 as a result of the member 70T being bent in the vicinity of the affected area 46. If it is assumed that the image pickup range of the first image pickup unit C11 moves upward in the drawing of FIG. 23 as a result of the extending member 70T being bent, a range including a range IR1ab in FIG. 23 is picked up by the first and the second image pickup units C11 and C12 before and after the member 70T is bent.

The control unit 11 can generate an image of the range IR1ab. The control unit 11 may cause the image of the range IR1ab to be displayed at the display unit 13, the FMD 15, or the like.

Figure 24:
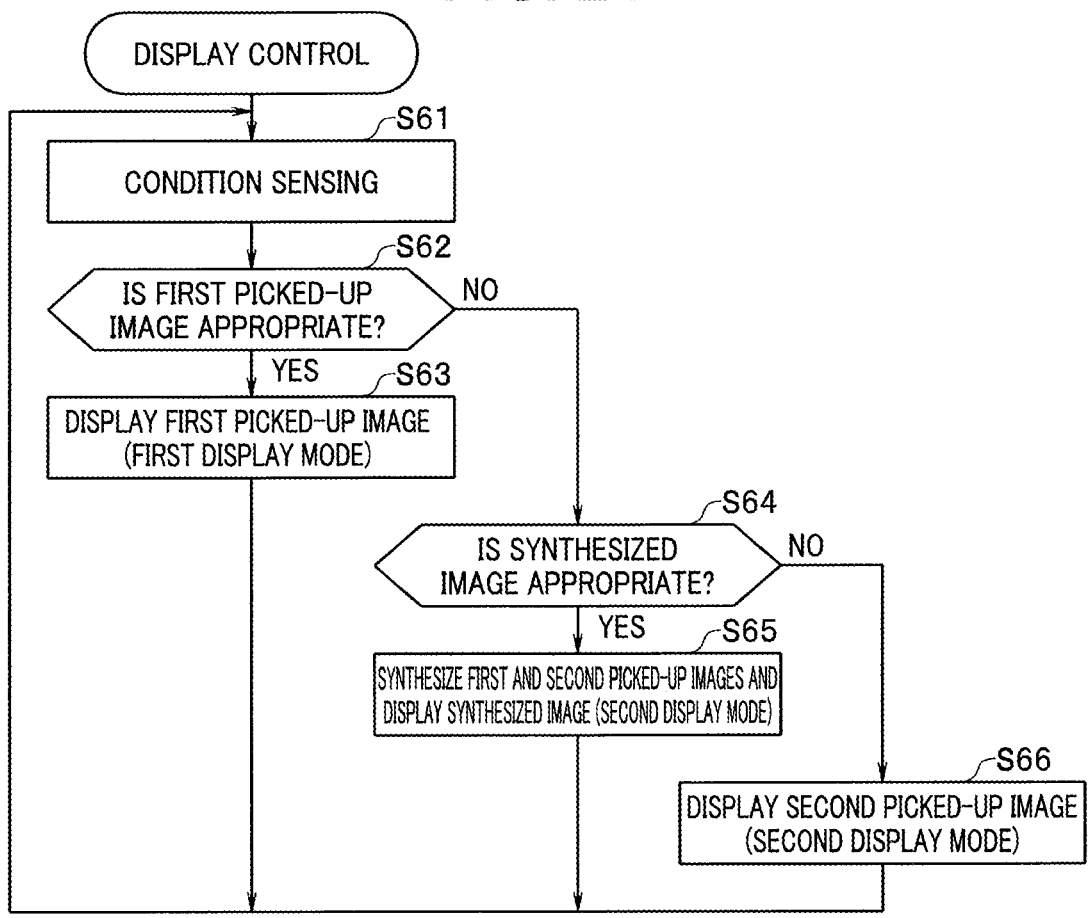
FIG. 24 is a flowchart for explaining operation of the fifth embodiment.

Operation of the embodiment configured in this manner will be described next with reference to FIG. 24. FIG. 24 is a flowchart for explaining operation of the fifth embodiment.

In step S61 in FIG. 24, the condition determination circuit 20 performs condition determination based on the detection results of the various kinds of sensors in a similar manner to the above-described embodiments (condition sensing). The condition determination circuit 20 may determine that the first display mode is appropriate during insertion of the insertion portion 70 and may determine that the second display mode is appropriate dining procedure in a similar manner to the above-described embodiments. Further, the condition determination circuit 20 may determine that display of a synthesized image of the first and the second picked-up images in the second display mode is preferable in a predetermined period from when bending of the member 70T is started, or as necessary.

As illustrated in FIG. 20, first, the surgeon inserts the insertion portion 70 toward the vicinity of the affected area 46. In this case, the condition determination circuit 20 determines that the first display mode in which the first picked-up image (sub image) from the first image pickup unit C11 provided at the distal end of the member 70T is used for display is appropriate. The control unit 11 displays the first picked-up image (sub image) from the first image pickup unit C11 at the FMD 15, the display unit 13, or the like (first display mode). As illustrated in FIG. 22, an image of an extremely wide image pickup range by the sub image is displayed at the FMD 15, or the like, which is appropriate for insertion work of the insertion portion 70.

The surgeon operates, for example, the manipulator to bend the member 70T as illustrated in FIG. 21 to facilitate observation of the affected area 46 and periphery of the affected area 46 when the distal end of the insertion portion 70 reaches the vicinity of the affected area 46. The condition determination circuit 20 determines that the member 70T is bent from, for example, change in the sub image from the first image pickup unit C11 if the surgeon performs operation of bending the member 70T with the manipulator and outputs a determination result indicating that display using the first picked-up image (sub image) is not preferable, and display of a synthesized image of the first and the second picked-up images is preferable to the control unit 11. Note that the condition determination circuit 20 may determine that the member 70T is bent by detecting that bending operation of the member 70T by the manipulator is performed by some kind of sensor.

The processing of the control unit 11 transitions from step S62 to step S64. The control unit 11 sets the second display mode by the determination result indicating that display of the synthesized image is preferable and provides the synthesized image of the first and the second picked-up images to the FMD 15, or the like, to cause the synthesized image to be displayed in step S64. By this means, the synthesized image of the second picked-up image by the second image pickup unit C12 disposed at a position facing the affected area 46 and of the first picked-up image by the first image pickup unit C11 that picks up an image of a wide range is displayed at the FMD 15, or the like, so that the surgeon can easily confirm basic work.

Here, it is assumed that the surgeon performs confirmation work of performing procedure on the affected area 46 with the treatment instrument 72. The condition determination circuit 20 determines that display in the second display mode using the second picked-up image (main image) is appropriate if start of the confirmation work is detected. By this means, the processing transitions from step S64 to step S66, and the control unit 11 causes the second picked-up image (main image) to be displayed at the FMD 15, or the like.

The condition determination circuit 20 determines whether the synthesized image is appropriate or a single image is appropriate through image analysis on the first and the second picked-up images from the first and the second image pickup units C11 and C12, for example, in accordance with to what extent the distal end portion 72*a* of the treatment instrument 72 is included in the first and the second picked-up images in determination in step S64.

For example, in a case where the distal end portion 72*a* of the treatment instrument 72 is located in a blind area of the first image pickup unit C11, the condition determination circuit 20 determines that the synthesized image of the first and the second picked-up images is appropriate. In this case, the control unit 11 generates the synthesized image of the first and the second picked-up images and causes the synthesized image to be displayed at the FMD 15, or the like, in the second display mode (step S65). In this manner, the surgeon can, for example, surely confirm the distal end portion 72*a*, or the like, in the second display mode using only the sub image or the synthesized image of the main image and the sub image. In this manner, the present embodiment can provide a display control apparatus that displays, in work on an object within a space, at least one of a first picked-up image by a first image pickup unit disposed at a first predetermined position within the space or a second picked-up image by a second image pickup unit disposed at a second predetermined position different from the first predetermined position within the space, in which the first image pickup unit is an image pickup unit provided for confirming spatial change in an insertion direction during insertion of an insertion member, in which the image pickup unit is provided, into the space, the second image pickup unit is an image pickup unit configured to detect change in an image based on work in work process on the object after the respective image pickup units are disposed at specific positions within the space by the insertion operation into the space, and the first image pickup unit has an image pickup range that allows observation of the object which is image-picked up by the second image pickup unit, allowing for a reliable display with fewer blind areas.

In this manner, in the present embodiment, effects similar to the effects of the above-described embodiments can be obtained. Further, in the present embodiment, the insertion portion is bent, so that procedure, or the like, on the affected area can be surely confirmed by the two image pickup units provided at the distal end of the insertion portion.

Note that also in the fifth embodiment, as in the embodiment in FIG. 8, the image pickup unit C11 may be provided on the side surface of the distal end of the insertion portion 70. Further, in the embodiment in FIG. 8, the insertion portion 1 may be bent between the image pickup units C1 and C2. Further, while the fifth embodiment illustrates an example where the member 70T is bent toward a side opposite to the side surface on which the image pickup unit C12 is disposed, the member 70T may be bent toward a side of the side surface on which the image pickup unit C12 is disposed or may be able to be bent in any direction in a radial direction of the insertion portion 70.

Further, while in the example in FIG. 20 and FIG. 21, the member 70T is not bent between the image pickup units C11 and C12, the member 70T may be bent between the image pickup units C11 and C12.

Figure 25:
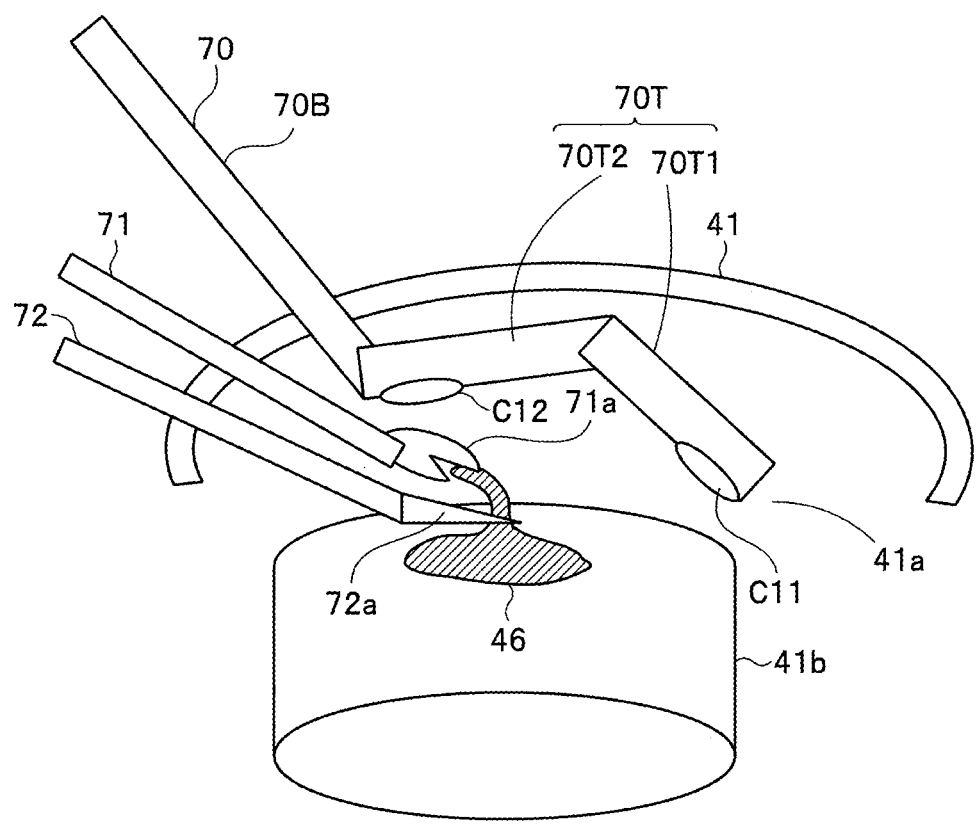
FIG. 25 is an explanatory diagram illustrating modification of the fifth embodiment.

FIG. 25 is an explanatory diagram illustrating an example of the case. In FIG. 25, the same reference numerals will be assigned to components that are the same as the components in FIG. 20 and FIG. 21, and description will be omitted.

The distal end member 70T of the insertion portion 70 is constituted with a first member 70T1 and a second member 70T2 and is constituted so as to be bent between the first member 70T1 and the second member 70T2, and between the second member 70T2 and a proximal end member 70B. The bending may be able to be controlled by operation of a manipulator (not illustrated) disposed on the proximal end side of the insertion portion 70.

In the example in FIG. 25, the first image pickup unit C11 is disposed on the side surface of the distal end of the first member 70T1, and the second image pickup unit C12 is disposed on the side surface on the proximal end side of the second member 70T2. Note that the first and the second image pickup units C11 and C12 may be respectively disposed on side surfaces on the distal end side and on the proximal end side of the first member 70T1.

According to such a configuration, the first and the second members 70T1 and 70T2 are bent, which makes a degree of freedom of change of the image pickup ranges of the first and the second image pickup units C11 and C12 extremely large, so that confirmation during insertion and confirmation during procedure on the affected area 46 become extremely easy. Further, the image pickup units are not limited to the two of the first and the second image pickup units C11 and C12, and a third image pickup unit or a greater number of image pickup units may be provided.

Figure 26:
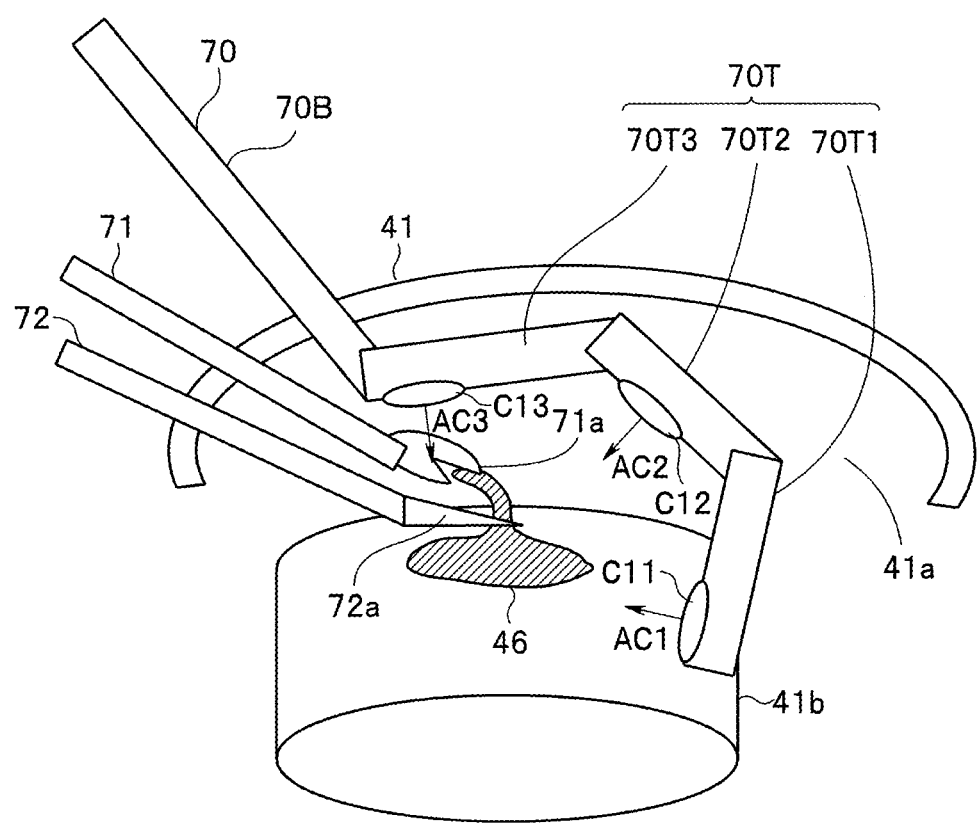
FIG. 26 is an explanatory diagram illustrating a modification of the fifth embodiment.

FIG. 26 is an explanatory diagram illustrating an example of a configuration in the case, and in FIG. 26, the same reference numerals will be assigned to components that are the same as the components in FIG. 20 and FIG. 21, and description will be omitted.

The distal end member 70T of the insertion portion 70 is constituted with the first member 70T1, the second member 70T2 and a third member 70T3 and is constituted so as to be bent at three portions between the first member 70T1 and the second member 70T2, between the second member 70T2 and the third member 70T3, and between the third member 70T3 and the proximal end member 70B. The bending may be able to be controlled by operation of a manipulator (not illustrated) disposed on the proximal end side of the insertion portion 70.

In the example in FIG. 26, the first image pickup unit C11 is disposed on the side surface of the distal end of the first member 70T1, the second image pickup unit C12 is disposed on the side surface on the proximal end side of the second member 70T2, and a third image pickup unit C13 is disposed on a side surface on the proximal end side of the third member 70T3. Note that the first to the third image pickup units C11 to C13 may be disposed at any positions of the first to the third members 70T1 to 70T3.

As illustrated in FIG. 26, line-of-sight directions of the first to the third image pickup units C11 to C13 are respectively directions AC1, AC2 and AC3, and the directions can be set at directions independent of each other in accordance with degrees of bending of the first to the third members. In this manner, the first to the third members 70T1 to 70T3 are bent, which makes a degree of freedom of change of the image pickup ranges of the first to the third image pickup units C11 to C13 extremely large, so that confirmation during insertion and confirmation during procedure on the affected area 46 become extremely easy.

Figure 27:
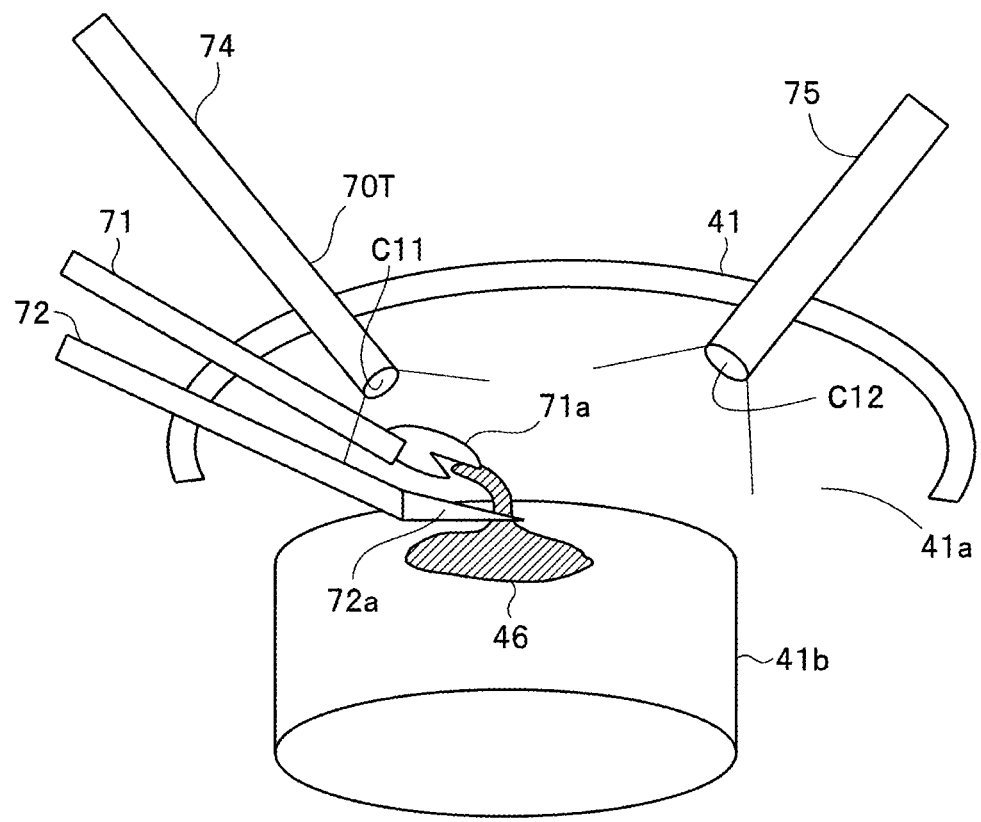
FIG. 27 is an explanatory diagram illustrating a modification of the fifth embodiment.

FIG. 27 illustrates a modification and illustrates an example where the first and the second image pickup units C11 and C12 are respectively provided at different insertion members 74 and 75. The insertion members 74 and 75 are constituted with, for example, an insertion portion of the endoscope. The first image pickup unit C11 is disposed at the distal end of the insertion member 74, and the second image pickup unit C12 is disposed at the distal end of the insertion member 75. The insertion members 74 and 75 are inserted into the abdominal cavity 41a from positions different from each other in the abdominal area 41. As a result, the image pickup range of the first image pickup unit C11 becomes different from the image pickup range of the second image pickup unit C12, so that images of regions that are blind areas of each other can be picked up.

Figure 28:
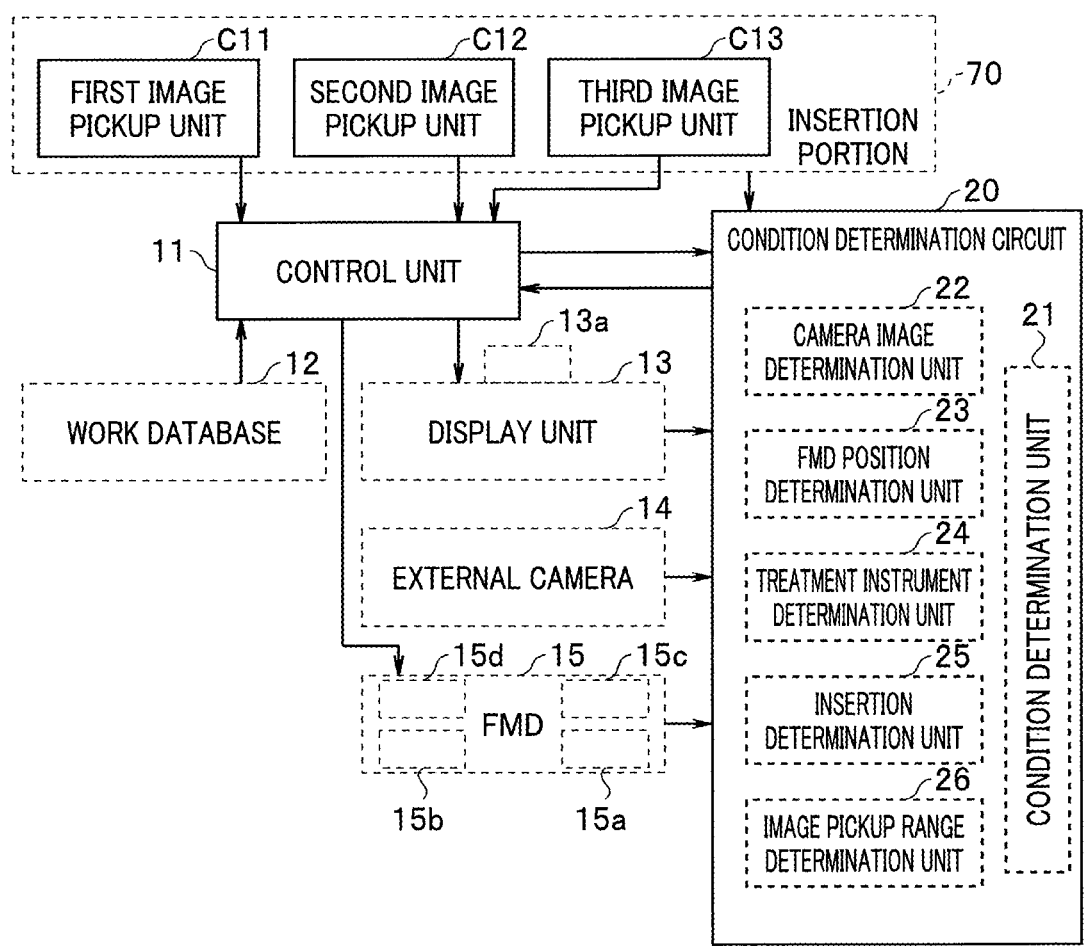
FIG. 28 is a block diagram illustrating a modification of a display control apparatus.

FIG. 28 is a block diagram illustrating a configuration in a case where three image pickup units are provided as in the example. In FIG. 27, the same reference numerals will be assigned to components that are the same as the components in FIG. 1, and description will be omitted.

FIG. 28 corresponds to the example in FIG. 26, and three image pickup units C11 to C13 are provided within the insertion portion 70. Picked-up images obtained by the respective image pickup units C11 to C13 are supplied to the control unit 11. Note that a direction sensor 15e is provided at the FMD 15.

FIG. 29 illustrates picked up images P11 to P13 respectively obtained by the image pickup units C11 to C13. The condition determination circuit 20 determines which of the picked-up images P11 to P13 is preferably used for display through various kinds of determination described above and outputs the determination result to the control unit 11. In other words, the condition determination circuit 20 outputs a determination result indicating that display is preferably performed using one main image among the picked-up images P11 to P13 or a determination result indicating that display is preferably performed by utilizing an image other than the main image among the picked-up images P11 to P13.

Note that in this case, the condition determination circuit 20 may detect a viewing direction of the surgeon by an output of the direction sensor 15e provided at the FMD 15 and may utilize the detection result in condition determination. For example, the condition determination circuit 20 may set the picked-up image obtained by the image pickup unit that picks up an image in a viewing direction closest to the viewing direction of the surgeon as the main image by comparing viewing directions A1 to A3 of the first to the third image pickup units C11 to C13 with the viewing direction of the surgeon.

The control unit 11 performs display control of the FMD 15 and the display unit 13 using the picked-up images P11 to P13 based on the determination result of the condition determination circuit 20.

Note that the control unit 11, the condition determination circuit 20, or the like, of the above-described embodiment may be constituted with a dedicated circuit or a combination of a plurality of general-purpose circuits and may be constituted with a combination of a processor such as a microprocessor that performs operation in accordance with software programmed in advance and a CPU or a sequencer. Further, design may be employed such that part or all of the control is performed by an external apparatus, in which case, a wired or wireless communication circuit intervenes. An embodiment in which characteristic processing and supplemental processing of the respective embodiments are performed by external equipment such as a server and a personal computer is also assumed. In other words, the present application also covers a case where features of the present invention are achieved by coordination of a plurality of pieces of equipment. Bluetooth (registered trademark), Wi-Fi (registered trademark), a phone line, or the like, is used for communication in the case. Further, the communication in the case may also be performed with a USB, or the like. The dedicated circuit, the general-purpose circuits and the control unit may be integrated to be constituted as an ASIC.

Further, most of control and functions described mainly using the flowchart among the technology described here can be constituted by a program, and the above-described control and functions can be implemented by a computer reading and executing the program. The whole or part of the program can be recorded or stored in a portable medium such as a non-volatile memory such as a flexible disk and a CD-ROM or a storage medium such as a hard disk and a volatile memory as a computer program product and can be distributed or provided upon shipment of the product by way of a portable medium or a communication line. A user can easily implement the display control apparatus of the present embodiment by downloading the program by way of a communication network and installing the program in a computer or installing the program in a computer from a recording medium.

The present invention is not limited to the above-described embodiments and can be embodied by modifying components within a range not deviating from the gist in an implementation phase. Further, various inventions can be made by appropriate combinations of a plurality of components disclosed in the above-described embodiments. For example, some components among all the components described in the embodiments may be deleted. Further, components across different embodiments may be combined as appropriate. While an example in medical use has been described here, it goes without saying that the present invention can be applied to industrial equipment if the equipment performs image pickup, inspection and procedure using an image pickup unit that enters a space that cannot be entered by an operator, as substitute for eyes. Further, while an example where the apparatus is inserted with the hand has been illustrated, an automatic insertion mechanism for insertion may be assumed, or the present invention may be utilized in application for switching images obtained through remote operation of a robot or a drone.

What is claimed is:

1. A display control apparatus comprising:
    a database configured to store information, for an operator who performs work on an object within a space outside the space, on characteristics of a posture or operation of basic work and characteristics of a posture or operation of confirmation work, and
    a processor; wherein
    the processor is configured to
    determine, in the work on the object within the space, which one of a first picked-up image by a first image pickup device disposed at a first predetermined position within the space and a second picked-up image by a second image pickup device disposed at a second predetermined position different from the first predetermined position within the space is appropriate for confirmation of procedure in a state associated with the work on the object using a treatment instrument, by detecting movement of the operator using an output of a third image pickup device configured to pick up an image of the operator who performs the work outside the space or an output of a sensor configured to detect movement of the operator, obtaining the characteristics of the posture or the operation of the basic work and the characteristics of the posture or the operation of the confirmation work based on the detection result, determining whether the operator is performing the basic work or the confirmation work by referring to the database using the characteristics obtained, and if it is determined that the operator is performing the confirmation work, determining which one of the first picked-up image and the second picked-up image is appropriate for confirmation of the procedure, and control display using at least one of the first picked-up image or the second picked-up image based on the determination result.

2. The display control apparatus according to claim 1, wherein
the processor is configured to obtain the determination result based on a detection result of movement of an operator who performs work using the treatment instrument outside the space.

3. The display control apparatus according to claim 1, wherein
the processor is configured to obtain the determination result based on a detection result of a position of an insertion member inserted into the space.

4. The display control apparatus according to claim 1, wherein
the processor is configured to obtain the determination result based on a picked-up image by at least one of the first image pickup device or the second image pickup device within the space.

5. The display control apparatus according to claim 1, wherein
the first and the second image pickup devices are attached to an insertion member to be inserted into the space and are sequentially inserted into the space and disposed by the insertion member being inserted into the space.

6. The display control apparatus according to claim 1, wherein
an image pickup range of the first image pickup device at least partially overlaps with an image pickup range of the second image pickup device.

7. The display control apparatus according to claim 6, wherein
a bending portion is provided, the bending portion being configured to allow the first and the second image pickup devices sequentially inserted into the space and disposed to be bent with respect to a direction of the insertion within the space.

8. The display control apparatus according to claim 6, wherein
a bending portion is provided between the first image pickup device and the second image pickup device that are sequentially inserted into the space and disposed.

9. The display control apparatus according to claim 1, wherein
the first and the second image pickup devices are two image pickup devices selected from a plurality of image pickup devices.

10. The display control apparatus according to claim 1, wherein
one of the first and the second image pickup devices is an image pickup device provided for confirming spatial change in an insertion direction during insertion of an insertion member into the space.

11. The display control apparatus according to claim 1, wherein
the first and the second image pickup devices are image pickup devices configured to detect change in an image based on work in a work process on the object after insertion operation of an insertion member in which the first and the second image pickup devices are provided into the space is performed and the first and the second image pickup devices are disposed at specific positions within the space.

12. The display control apparatus according to claim 1, wherein
the work is work of changing positions of the first and the second image pickup devices within the space while displaying at least one of the first picked-up image or the second picked-up image or work of preventing creation of a blind area upon confirmation of change in a position of an instrument that enters image pickup ranges of the image pickup devices with respect to the object.

13. The display control apparatus according to claim 1, wherein
in a case where a determination result indicating that one of the first and the second picked-up images is not appropriate for the observation is obtained, the processor is configured to perform display including at least another picked-up image out of the first and the second picked-up images.

14. The display control apparatus according to claim 13, wherein
in a case where a determination result indicating that one of the first and the second picked-up images is not appropriate for the observation is obtained, the processor is configured to perform display using only another picked-up image out of the first and the second picked-up images.

15. The display control apparatus according to claim 13, wherein
in a case where a determination result indicating that one of the first and the second picked-up images is not appropriate for the observation is obtained, the processor is configured to display a synthesized image of the first and the second picked-up images.

16. The display control apparatus according to claim 1, wherein
the processor is configured to obtain the determination result based on an output of a third image pickup device configured to pick up an image of an operator who performs work outside the space or an output of a sensor configured to detect movement of the operator.

17. The display control apparatus according to claim 1, wherein
the processor is configured to obtain the determination result based on an output of a sensor configured to detect a position of the insertion member.

18. The display control apparatus according to claim 1, wherein
the processor is configured to obtain the determination result through image analysis on at least one of the first picked-up image or the second picked-up image.

19. The display control apparatus according to claim 18, wherein
the processor is configured to obtain the determination result based on an analysis result of an image in at least one of the first picked-up image or the second picked-up image, the image being of an instrument used for the work on the object.

20. The display control apparatus according to claim 6, wherein
the first image pickup device is disposed at a distal end of the insertion member.

21. The display control apparatus according to claim 20, wherein
the first picked-up image is displayed during work of inserting the insertion member into the space.

22. The display control apparatus according to claim 20, wherein
the second picked-up image is displayed when the work on the object is confirmed.

23. The display control apparatus according to claim 1, wherein
the processor is configured to obtain the determination result by performing image analysis on one picked-up image out of the first and the second image pickup devices to estimate an image pickup range of another picked-up image out of the first and the second image pickup devices.

24. A display control method using a database configured to store information, for an operator who performs work on an object within a space outside the space, on characteristics of a posture or operation of basic work and characteristics of a posture or operation of confirmation work, the method comprising:
determining, in the work on the object within the space, which one of a first picked-up image by a first image pickup device disposed at a first predetermined position within the space and a second picked-up image by a second image pickup device disposed at a second predetermined position different from the first predetermined position within the space is appropriate for confirmation of procedure in a state associated with the work on the object using a treatment instrument, by detecting movement of the operator using an output of a third image pickup device configured to pick up an image of the operator who performs the work outside the space or an output of a sensor configured to detect movement of the operator, obtaining the characteristics of the posture or the operation of the basic work and the characteristics of the posture or the operation of the confirmation work based on the detection result, determining whether the operator is performing the basic work or the confirmation work by referring to the database using the characteristics obtained, and if it is determined that the operator is performing the confirmation work, determining which one of the first picked-up image and the second picked-up image is appropriate for confirmation of the procedure, and
controlling display using at least one of the first picked-up image or the second picked-up image based on the determination result.

25. A non-transitory recording medium on which a display control program is recorded, the display control program causing a computer to execute:
determining, in the work on the object within the space, which one of a first picked-up image by a first image pickup device disposed at a first predetermined position within the space and a second picked-up image by a second image pickup device disposed at a second predetermined position different from the first predetermined position within the space is appropriate for confirmation of procedure in a state associated with the work on the object using a treatment instrument, by detecting movement of the operator using an output of a third image pickup device configured to pick up an image of the operator who performs the work outside the space or an output of a sensor configured to detect movement of the operator, obtaining the characteristics of the posture or the operation of the basic work and the characteristics of the posture or the operation of the confirmation work based on the detection result, determining whether the operator is performing the basic work or the confirmation work by referring to the database using the characteristics obtained, and if it is determined that the operator is performing the confirmation work, determining which one of the first picked-up image and the second picked-up image is appropriate for confirmation of the procedure, and
controlling display using at least one of the first picked-up image or the second picked-up image based on the determination result.

* * * * *